(12) United States Patent
Akudugu et al.

(10) Patent No.: US 9,804,167 B2
(45) Date of Patent: Oct. 31, 2017

(54) METHOD OF OVERCOMING THERAPEUTIC LIMITATIONS OF NONUNIFORM DISTRIBUTION OF RADIOPHARMACEUTICALS AND CHEMOTHERAPY DRUGS

(71) Applicant: Rutgers, The State University of New Jersey, New Brunswick, NJ (US)

(72) Inventors: John M. Akudugu, Bellville (ZA); Venkata S. Neti, Lake Hiawatha, NJ (US); Roger W. Howell, Millington, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 241 days.

(21) Appl. No.: 14/526,041

(22) Filed: Oct. 28, 2014

(65) Prior Publication Data

US 2015/0265730 A1    Sep. 24, 2015

Related U.S. Application Data

(62) Division of application No. 13/315,775, filed on Dec. 9, 2011, now Pat. No. 8,874,380.

(60) Provisional application No. 61/466,151, filed on Mar. 22, 2011, provisional application No. 61/421,491, filed on Dec. 9, 2010.

(51) Int. Cl.
| | |
|---|---|
| *G01N 33/60* | (2006.01) |
| *G01N 33/50* | (2006.01) |
| *A61K 31/704* | (2006.01) |
| *A61K 51/04* | (2006.01) |
| *A61K 51/10* | (2006.01) |

(52) U.S. Cl.
CPC ........... *G01N 33/60* (2013.01); *A61K 31/704* (2013.01); *A61K 51/0402* (2013.01); *A61K 51/1051* (2013.01); *G01N 33/5008* (2013.01); *G01N 33/5011* (2013.01)

(58) Field of Classification Search
CPC ..................................................... G01N 33/60
USPC ........................................................ 702/21
See application file for complete search history.

(56) References Cited

U.S. PATENT DOCUMENTS

| | | | |
|---|---|---|---|
| 5,229,275 A | 7/1993 | Goroff | |
| 5,545,806 A | 8/1996 | Lonberg et al. | |
| 5,545,807 A | 8/1996 | Surani et al. | |
| 5,567,610 A | 10/1996 | Borrebaeck et al. | |
| 5,569,825 A | 10/1996 | Lonberg et al. | |
| 5,591,669 A | 1/1997 | Krimpenfort et al. | |
| 5,871,907 A | 2/1999 | Winter et al. | |
| 6,699,473 B2 | 3/2004 | Raisch et al. | |
| 2003/0130496 A1 | 7/2003 | Winter et al. | |
| 2012/0107234 A1 | 5/2012 | Pedersen et al. | |

FOREIGN PATENT DOCUMENTS

| | | |
|---|---|---|
| WO | 93/11161 | 6/1993 |
| WO | 97/17852 | 5/1997 |

OTHER PUBLICATIONS

Li et al., "Feasibility of Eradication of Breast Cancer Cells Remaining in Postlumpectomy Cavity and Draining Lymph Nodes Following Intracavity Injection of Radioactive Immunoliposomes" Molecular Pharmaceutics, 2012, vol. 9, pp. 2513-2522.
Koch et al., "Oxygen Dependence of Cellular Uptake of EF5 [2-(2-nitro-1H-imidazol-1-yl)-N-(2,2,3,3,3-pentafluoropropyl)acetemide]: Analysis of Drug Adducts by Fluorescent Antibodies vs Boundy Raidoactivity," British J of Cancer, 1995, vol. 72, pp. 869-874.
Akudugu et al., "Changes in lognormal shape parameter guide design of patient-specific radiochemotherapy cocktails," J Nucl Med., (2011) vol. 52, pp. 642-649.
Akudugu et al., "Flow cytometry-assisted Monte Carlo simulation predicts clonogenic survival of cell populations with lognormal distributions of radiopharmaceuticals and anticancer drugs," Int J Radiat Biol., (2011) vol. 88, pp. 286-293 (Abstract only).
Brennan et al., "Preparation of bispecific antibodies by chemical recombination of monoclonal immunoglobulin G1 fragments," Science, (1985) vol. 229, p. 81-83 (Abstract only).
Carter et al., "High level *Escherichia coli* expression and production of a bivalent humanized antibody fragment," Biotechnology (1992) vol. 10, pp. 163-167 (Abstract only).
Deutscher, editor, "Guide to Protein Purification" in Methods in Enzymology (1990) Academic Press, Inc. (Synopsis only).
Freshney, "Culture of Animal Cells: A Manual of Basic Technique," 2nd Ed. (1987), Liss, Inc. New York, NY (Synopsis only).
Georgiou, et al., "Display of heterologous proteins on the surface of microorganisms: Fromn the screening of combinatorial libraries to live recominant vaccines," Nature Biotechnology, (1997) vol. 15, pp. 29-34.
Graham et al., "Manipulation of adenovirus vector," in "Gene Transfer and Expression Protocols," The Humana Press Inc., Clifton, NJ (1991) E. J. Murray, editor, vol. 7, pp. 109-128 (Synopsis of book only).
Hanes and Pluckthun, "In Vitro selection and evolution of functional proteins by using ribosome display," Proc. Nat. Acad. Sci. (1997) vol. 94, p. 4937-4942.
Hollinger et al., "'Diabodies': small bivalent and bispecific antibody fragments," Proc. Natl. Acad. Sci. USA, (1993) vol. 90, pp. 6444-6448 (Abstract only).

(Continued)

*Primary Examiner* — Jerry Lin
(74) *Attorney, Agent, or Firm* — Fox Rothschild LLP

(57) ABSTRACT

Disclosed is a method for predicting the optimal amounts of radiopharmaceutical and/or chemotherapy agents to administer to a patient, by determining the level of saturation of the therapeutic agents in the patient's cells. The method comprises measuring cellular incorporation of the candidate therapeutic agents in a target cell population on a cell-by-cell basis. The method is able to identify an optimal cocktail of therapeutic agents for treatment of a disease. A method of high-throughput drug discovery incorporating this method, and a 2-stage targeting method of treating a disease using this method are also disclosed.

10 Claims, 12 Drawing Sheets

(56) References Cited

OTHER PUBLICATIONS

Innis et al. (editors), "PCR Protocols: A Guide to Methods and Applications," (1990) Academic Press, San Diego, CA (Synopsis of book only).
Jakobovits et al., "Germ-line transmission and expression of a human-derived yeast artificial chromosome," Nature, (1993) vol. 362, pp. 255-258 (Abstract only).
Jakobovits et al., "Analysis of homozygous mutant chimeric mice: deletion of the immunoglobulin heavy-chain joining region blocks B-cell development and antibody production," Proc. Nat'l Acad Sci, USA, (1993) vol. 90, pp. 2551.
Jones et al., "Replacing the complementarity-determining regions in a human antibody with those from a mouse," Nature, (1986) vol. 321, pp. 522-525 (Abstract only).
Kabat et al., "Sequences of Proteins of Immunological Interest," 5th Ed. Public Health Service, National Institutes of Health Bethesda, Md. (1991) (Abstract only).
Kieke, et al., "Isolation of anti-T cell receptor scFv mutants by yeast surface display," Protein Engineering, (1997) vol. 10, pp. 1303-1310.
Morimoto et al., "Single-step purification of F(ab')2 fragments of mouse momoclonal antibodies (immunoglobulins G1) by hydrophobic interaction high performance liquid chromotography using TSKgel Phynel-5PW," Journal of Biochemical and Biophysical Methods, (1992) vol. 24, pp. 107-117.
Morrison et al., "Replacing the complementarity-determining regions in a human antibody with those from a mouse," Proc. Natl. Acad. Sci. USA, (1984) vol. 81, pp. 6851-6855.
Pluckthun et al., "The Pharmacology of Monoclonal Antibodies," (1994) Rosenburg and Moore eds, Springer-Verlag, New York, vol. 113, pp. 269-315.
Reichmann et al., "Reshaping human antibodies for therapy," Nature, (1988) vol. 332; pp. 323-327.
Sambrook et al., Molecular Cloning: A Laboratory Manual, (1989) Cold Spring Harbor Laboratory Press (Description only).
Vaughn, et al., "Human Antibodies with Sub-nanomolar Affinities Isolated form a Large Non-immunized Phage Display Library," Nature Biotechnology, (1996) vol. 14, pp. 309-314 (Abstract only).
Verhoeyen et al., "Reshaping human antibodies: grafting an antilysozyme activity," Science (1988), vol. 239, pp. 1534-1536 (Abstract only).
Zapata et al., "Engineering linear F(ab')2 fragments for efficient production in *Escherichia coli* and enhanced antiproliferative activity," Protein Eng. (1995) vol. 8, Issue 10, pp. 1057-1062 (Abstract only).
U.S. Appl. No. 13/315,775, filed Dec. 9, 2011, Method of Overcoming Therapeutic Limitations of Nonuniform Distribution of Radiopharmaceuticals and Chemotherapy Drugs.
U.S. Appl. No. 13/953,414, filed Jul. 29, 2013, Antibody Cocktails for Breast Cancer Radioimmunotherapy.

STEP 1

Flow cytometry measurement of drug uptake $I_i$

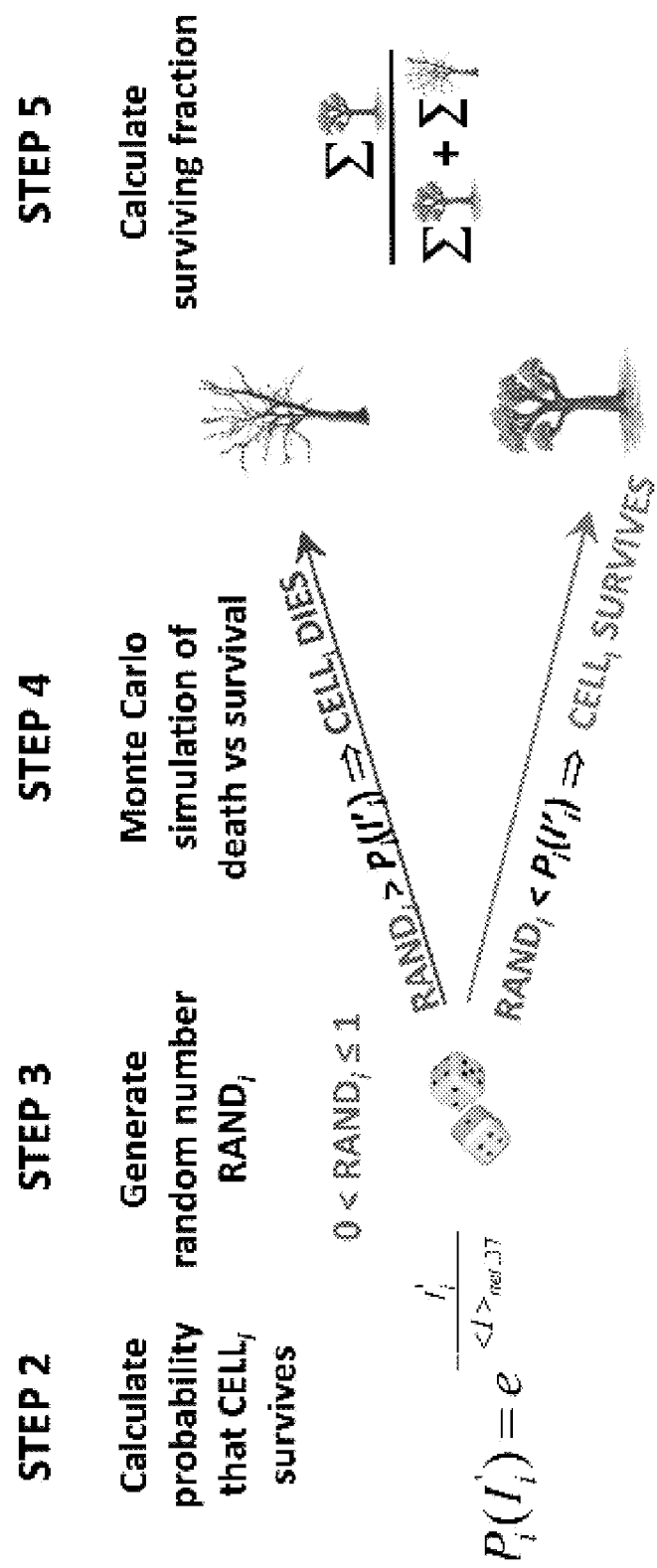
FIGURE 5 - Continued

STEP 1

Flow cytometry measurement of drug uptake $I_i$

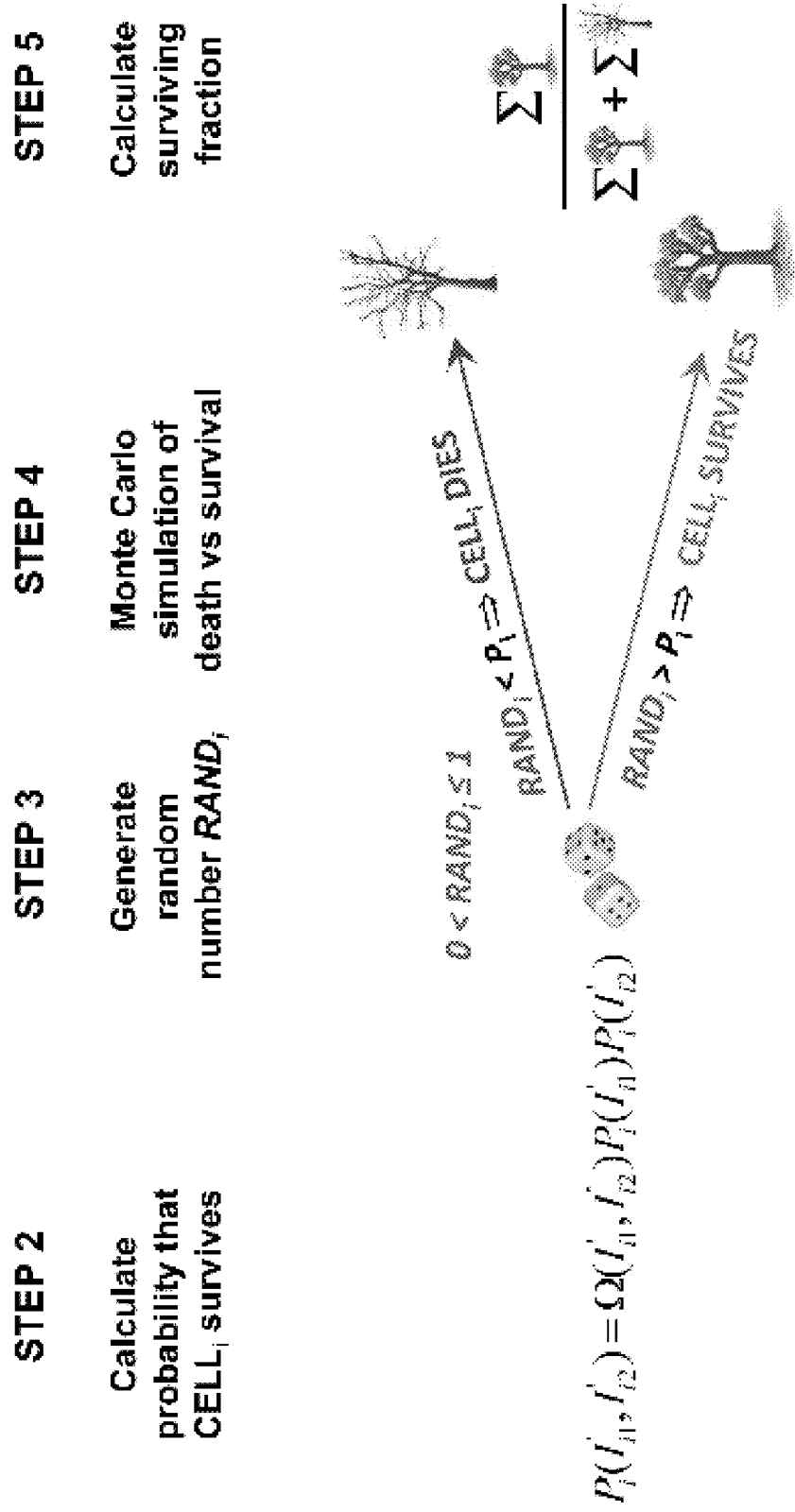
FIGURE 8 - Continued

METHOD OF OVERCOMING THERAPEUTIC LIMITATIONS OF NONUNIFORM DISTRIBUTION OF RADIOPHARMACEUTICALS AND CHEMOTHERAPY DRUGS

CROSS-REFERENCE TO RELATED APPLICATIONS

The present application is a divisional of U.S. Ser. No. 13/315,775, filed Dec. 9, 2011 and granted on Oct. 28, 2014 as U.S. Pat. No. 8,874,380 which claims the benefit of priority under 35 U.S.C. 35 §119(e) to US Provisional Applications No. 61/466,151 filed on Mar. 22, 2011, and 61/421,491 filed on Dec. 9, 2010, the disclosures of which are all incorporated by reference in their entireties.

STATEMENT REGARDING FEDERALLY SPONSORED RESEARCH OR DEVELOPMENT

The invention was made with government support under Contract No. R01 CA083838 awarded by NIH/NCI. The government has certain rights in the invention.

FIELD OF THE INVENTION

The present invention relates to a novel method for formulating cocktails of therapeutic agents and predicting the optimal amount of each constituent radiopharmaceutical and/or chemotherapy agent to administer to a patient, by determining the level of cell saturation of these agents and by simulating cell death and surviving fraction, preferably using Monte Carlo methods.

BACKGROUND OF THE INVENTION

The use of chemotherapeutic drugs as an adjuvant to external beam radiotherapy, surgery, or other treatment modalities is common practice for the treatment of a wide variety of solid tumors. This approach has demonstrated some success in the management of certain cancers. The rationale for combining chemotherapeutic agents with external beam radiotherapy is to radiosensitize the irradiated tumor tissue and/or to target subpopulations of malignant cells that have metastasized from the primary lesion demarcated for beam therapy. Although the tradition of chemoradiotherapy has been practiced for decades and shows promise, some attempts have not succeeded in demonstrating either an added therapeutic benefit or a reduction of normal tissue toxicity. In another approach, radiolabeled chemotherapy agents have been used in an attempt to achieve enhanced cytotoxicity both in human cancer cells and apparently normal hamster fibroblasts. Chemotherapy has also been combined with radioimmunotherapy.

One limitation of chemoradiotherapy is the frequent lack of interaction between chemotherapeutics and ionizing radiation. This often leads to escalation of radiation and drug doses, which in turn, results in elevated normal tissue toxicity. Moreover, lack of specificity of chemotherapy drugs for tumor tissue can result in an insignificant difference in toxicity towards malignant and normal tissues thereby providing no added therapeutic benefit compared to surgery and radiation alone. Despite these limitations, chemoradiotherapy often provides considerable therapeutic benefit. However, observed inconsistencies in treatment outcomes may be due to the widely varying chemotherapeutic drug concentrations employed and radiation absorbed doses achieved. In addition, there is evidence demonstrating that optimization of radiation dose and drug concentration, and the time sequence for administering drugs and radiation play important roles in treatment responses both in vitro and in vivo. Also, regardless of the quality of radiation used, the wide variability in drug toxicity in normal cells of different histologies has to be considered in favor of the most sensitive tissue in chemoradiotherapy. Unfavorable outcomes in therapies involving the use of chemotherapy drugs and radiopharmaceuticals have been attributed to insufficient tumor specificity, poor tumor vascularization, and nonuniformities in agent distribution at the macroscopic, cellular, and subcellular levels. Determination of drug and radionuclide incorporation at the single-cell level has been difficult. As such, estimation of intracellular chemotherapy drug concentration and intra-cellular radioactivity (required to determine radiation absorbed dose to the cell) has largely been restricted to the macroscopic level. Accordingly, it has been difficult to establish a relationship between therapeutic agent incorporation and biologic response.

It has now been discovered that, even in situations where there is optimum perfusion and no diffusion barriers, cellular incorporation of radionuclides and chemotherapeutic drugs is not only nonuniform, but is also lognormal. This strongly suggests that the limited success in chemoradiotherapy of primary solid tumors and metastatic disease is likely due to this lognormal phenomenon, in which minute subpopulations of cells take up very little or no therapeutic agent. Repopulation by these subpopulations could mask a possible treatment benefit and result in an even more resistant neoplastic form. Thus, to enhance tumor response, there continues to be a need to address the nonuniform, lognormal distribution of chemotherapy drugs and radiopharmaceuticals. Using a quantitative immunofluorescence-based approach, it has now been demonstrated in a 3-dimensional culture system that concomitant measurement of radiopharmaceutical uptake and biologic response in individual cells within a population can be used to predict the response of subpopulations of cells, and ultimately of the entire population. Such capabilities now allow the design of more effective cocktails for clinical applications.

BRIEF SUMMARY OF THE INVENTION

One aspect of the present invention relates to a novel method for predicting the optimal amount of radiopharmaceutical and chemotherapy agents to administer to a patient, by determining the level of cell saturation. This includes a method of predicting the response of an individual patient's disease to therapeutic intervention with radiopharmaceuticals, chemotherapeutics, targeted therapeutics such as radiolabeled monoclonal antibodies, or other agents. Specifically, cellular incorporation of therapeutic agents is measured in the target cell population on a cell-by-cell basis using a flow cytometer. The resulting fluorescence spectra are fitted to the lognormal probability density function to obtain the lognormal shape parameter, σ, also known as the standard deviation, for each treated sample. Surprisingly it has been discovered that: (1) changes in the lognormal shape parameter, σ, upon exposure of the cells to increasing drug concentrations, correlate with changes in the shape of the cell survival curve, and therefore can identify the optimal drug concentration for use in a drug cocktail; (2) the surviving fraction of a target cell population exposed to the therapeutic agent can be predicted using a flow-cytometry assisted Monte Carlo simulation that accounts for the lognormal characteristics of the distribution; and (3) the optimal cocktail of therapeutic drugs can be identified by exposing target cells to combinations of drugs, whereby the optimal concentration of each drug is identified using (1), by employing flow cytometry to simultaneously measure the uptake of each drug, then simulating the surviving fraction of the target population using (2), and using the simulated results to identify the combination of drugs that affords the optimum degree of killing of the target cells. (1) and (2) have been demonstrated with a radiochemical ($^{210}$Po-citrate) and two anticancer drugs (daunomycin and doxorubicin) in Chinese hamster V79 cells. (3) has been demonstrated with a combination of $^{210}$Po and daunomycin and a combination of $^{210}$Po and doxorubicin. Another aspect of the invention provides patient-specific cocktail formulations by identifying existing drugs that can be added to a cocktail to facilitate targeting subpopulations of cells that would otherwise escape targeting.

One embodiment of the invention is directed to a method for predicting the response of an individual patient's cells, which preferably comprise cancer cells, to therapeutic intervention, comprising the steps of:
(a) exposing populations of said cells to increasing concentrations of a candidate therapeutic agent for said condition;
(b) measuring the incorporation of said therapeutic agent in said populations on a cell-by-cell basis, preferably employing a high-speed technique, preferably flow cytometry, with the incorporation being measured using fluorescence spectroscopy, preferably using a combination of individual cell fluorescence intensities and mean fluorescence intensity (MFI);
(c) plotting the number of cells versus the amount of incorporated therapeutic agent, to obtain distribution plots for said populations;
(d) fitting said distribution plots to a probability density function, preferably a lognormal function, to obtain a distribution curve and the standard deviation, $\sigma$, for each population; and
(e) identifying the optimal concentration of said therapeutic agent for said patient by identifying changes in the slope of a plot of $\sigma$ as a function of concentration of said therapeutic agent.

The method may further comprise the steps of determining the surviving fraction of cells, plotting the surviving fraction versus the amount of incorporated therapeutic agent, and fitting the plot to a probability function, preferably selected from the group of functions consisting of exponential and linear-quadratic. Preferably, the method also further comprises the step of predicting the surviving fraction of said cell populations using a simulation, preferably a Monte Carlo simulation, that accounts for the characteristics of said distribution curve, preferably flow-cytometry assisted Monte Carlo simulation.

A specific embodiment is directed to a method for predicting the response an individual patient's cancer cells to therapeutic intervention.

Another embodiment of the method includes exposing the cells to increasing concentrations of a plurality of therapeutic agents, and identifying an effective combination of therapeutic agents as well as the optimal concentration of each drug/therapeutic agent.

Another embodiment of the invention is directed to a method of high-throughput drug discovery comprising the above method for predicting the response of an individual patient's cells to therapeutic intervention.

Yet another embodiment of the invention is directed to a 2-stage targeting method of treating a disease or condition for a patient in need thereof, the method comprising:
(1) identifying and providing a plurality of candidate targeting agents relevant to the disease or condition of said patient, wherein said targeting agents are two-stage agents comprising:
(a) Stage 1 agents which are non-toxic and target the diseased or affected cells; and
(b) Stage 2 agents which bind to said Stage 1 agents and carry at least one additional agent selected from the group consisting of toxins, radionuclides and fluorochromes, wherein each Stage 2 agent can only bind to a single corresponding Stage 1 agent;
(2) injecting said patient with a cocktail of Stage 1 agents via a route appropriate to said disease or condition, and allowing sufficient time for maximum uptake by said diseased or affected cells and substantial clearance of unbound Stage 1 agents;
(3) withdrawing a sample of said patient's diseased or affected cells loaded with Stage 1 agents;
(4) treating said sample of said cells in vitro with a cocktail of said Stage 2 agents, wherein each Stage 2 agent carries a unique fluorochrome, and wherein said Stage 2 agents bind to said Stage 1 agents loaded into said cells;
(5) quantifying the amount of each Stage 2 agent binding to each diseased or affected cell using fluorescence spectroscopy;
(6) predicting the response of said diseased or affected cells for every possible combination of Stage 1 and Stage 2 agents using the above method for predicting the response of an individual patient's cells to account for the lognormal distribution of each agent, and identifying the optimal combination of said agents;
(7) arming each Stage 2 agent of said optimal combination with one or more therapeutic agents selected from the group consisting of toxins, radionuclides, other molecular therapeutics, and combinations of two or more thereof, to form an armed cocktail;
(8) optionally, repeating step (2); and
(9) injecting said armed cocktail into said patient.

The method may further comprise repeating steps (3) through (6) with normal or healthy cells of said patient in place of diseased/affected cells, in order to assess the uptake of said Stage 1 and Stage 2 agents in each normal/healthy cell.

A further embodiment of the invention is directed to a computational method for processing the above-indicated data, including flow cytometry data, in order to determine the parameter $\sigma$ and calculate therefrom the optimal dose, or effective dose, of each component of the drug cocktail.

DETAILED DESCRIPTION OF PREFERRED EMBODIMENTS

Figures 1A, 1B:
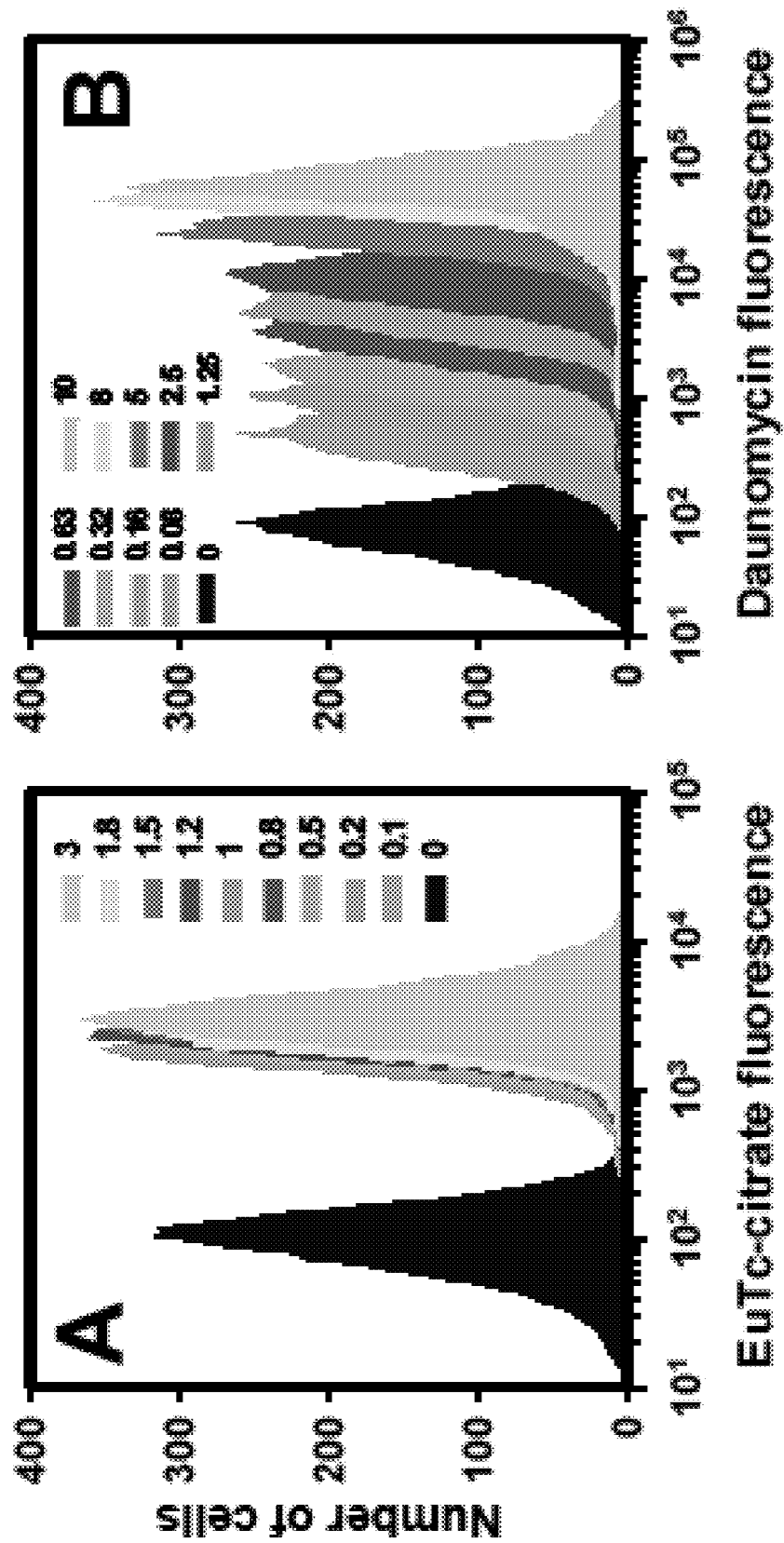
FIG. 1 shows the distribution of cellular uptake of citrate, daunomycin, and doxorubicin by V79 cells in a suspension culture. Displayed are representative flow cytometry generated histograms of cellular fluorescence intensity after treatment with 0-3 mmol/L EuTc-citrate (A), 0-10 μmol/L daunomycin (B), or 0-10 μmol/L doxorubicin (C).

The therapeutic significance of nonuniform incorporation of chemotherapy drugs and radiopharmaceuticals by cancer cells has been recognized as an issue of long standing in the art. Yet, the impact of lognormal drug distributions on the capacity of an agent to sterilize a population of cells has not been previously recognized. A small lognormal shape parameter (σ) implies a narrow distribution profile, and σ approaches zero when all cells incorporate the same amount of agent. On the other hand, a large σ signifies a wide spread in distribution, and agent incorporation may range from very low (potentially nontoxic) to high (lethal). The ubiquity of lognormal drug distributions has now been demonstrated by using flow cytometry to assess the distribution of radionuclides, for example, $^{210}$Po-citrate, and pharmaceutical agents, for example, daunomycin, and doxorubicin. Equally important is the discovery that changes in the value of σ as a function of increasing drug concentration parallel marked changes in the shapes of the corresponding clonogenic cell survival curves. Further, surprisingly it has now been discovered that experimental lognormal distributions (i.e. individual drug uptake on a cell-by-cell basis) can be used to accurately predict the saturation that is observed in experimental cell survival-curves (e.g. two-component exponential curves). This saturation has now been observed repeatedly in studies on the lethal effects of nonuniform distributions of radioactivity. Furthermore, theoretical studies now show that lognormal distributions can lead to such two-component exponential survival curves in both monolayer and three-dimensional tissue constructs.

The overall biological response must be influenced by the magnitude of the mean cellular drug uptake and the degree of heterogeneity in agent distribution. Therefore, a change in the capacity of an agent to sterilize a cell population is related to both the change in width of the distribution and the peak-shift as the agent concentration increases. While the former is a measure of the broadness of a distribution profile of the agent among a cell population and can be represented by the lognormal shape parameter, σ, the latter is a shift in the lognormal scale parameter μ which is an indication of cells accumulating increasing levels of the agent. Changes in σ are prognostic of whether a survival curve will exhibit saturation, and that σ may guide in the selection of agents for multimodality cocktail design by providing information on agent concentrations at which the first component of cell kill ends. However, the shape parameter only describes the agent distribution profile of the cell population as a whole, but does not provide information on the fate of individual cells of the population.

Surprisingly, it has also now been discovered that clonogenic cell survival can be predicted based only on knowledge of the initial slope of the cell survival curve and information on the distribution of agent incorporation among the treated cell population. For example, the distribution of $^{210}$Po, daunomycin and doxorubicin among populations of Chinese hamster V79 cells was assessed using flow cytometry techniques and used to theoretically model the surviving fraction. Several modeling approaches were compared, including flow-cytometry gating of agent-negative cells, Monte Carlo simulation of cell survival based on the experimental distributions of drug uptake, and Monte Carlo simulation of cell survival based on the more conventional approach of using mean cellular uptake of the drugs.

It has now been demonstrated that Monte Carlo simulation using cellular agent incorporation based on individual cell fluorescence intensity of therapeutic agents is a suitable predictor of cell survival. This flow cytometry based approach, which takes explicit account of the lognormal distribution of cellular uptake of the agents, offers a rapid means for determining treatment response on a cell-by-cell basis, and allows the selection of agents for the design of highly effective therapeutic cocktails that are capable of targeting the diversity in tumor cell populations. Such cocktails can be created not only for treatment of cancer, but also for infectious diseases and other diseases that may be amenable to targeted therapies. Furthermore, this single-cell Monte Carlo technique can be used to resolve difficulties encountered when attempting to predict biological response at the multicellular level using macroscopic mean agent doses.

A first embodiment of the invention is directed to a method for predicting the response of an individual patient's cells to therapeutic intervention comprising the steps of:
  (a) exposing populations of said cells to increasing concentrations of a candidate therapeutic agent for said condition;
  (b) measuring the incorporation of said therapeutic agent in said populations on a cell-by-cell basis, preferably employing a high-speed technique, preferably flow cytometry, with the incorporation being measured using fluorescence spectroscopy, preferably the individual cell fluorescence intensities and the mean fluorescence intensity (MFI);
  (c) plotting the number of cells versus the amount of incorporated therapeutic agent, to obtain distribution plots for said populations;
  (d) fitting said distribution plots to a probability density function, preferably a lognormal function, to obtain a distribution curve and the standard deviation, σ, for each population; and
  (e) identifying the optimal concentration of said therapeutic agent for said patient by identifying changes in the slope of a plot of σ as a function of concentration of said therapeutic agent.

The method may further comprise the steps of determining the surviving fraction of cells, plotting the surviving fraction versus the amount of incorporated therapeutic agent, and fitting the plot to a probability function, preferably selected from the group of functions consisting of exponential and linear-quadratic. Preferably, the method also further comprises the step of predicting the surviving fraction of said cell populations using a simulation, preferably a Monte Carlo simulation, that accounts for the characteristics of said distribution curve, preferably flow-cytometry assisted Monte Carlo simulation.

In a further embodiment of the invention, cells are exposed to increasing concentrations of a plurality of therapeutic agents, and the optimal concentration of each drug is identified. The simulation results are then used to identify an effective combination of therapeutic agents in their therapeutically effective amounts.

The biological targets of the method include cells with uncontrolled growth, such as tumor cells, or cells infected with pathogens, including without limitation, bacteria, viruses, prions, and parasites. The biological target may also include stem cells. In a preferred embodiment of the method, the individual patient's cells comprise cancer cells.

The therapeutic agents comprise, without limitation, antibodies, peptides, chemo-therapeutics, radiopharmaceuticals, antifungals, antibiotics and other pharmaceuticals.

Any high-speed technique for assaying drug uptake on a cell-by-cell basis, as known in the art, can be used, including, without limitation, microfluidic techniques such as flow cytometry and microfluidic impedance cytometry; laser scanning microscopy; and gas chromatography/mass spectrometry (GC/MS). Preferably, the high-speed technique for assaying therapeutic agent uptake on a cell-by-cell basis comprises flow cytometry. The analytical method used to determine the incorporation of therapeutic agent preferably comprises fluorescence spectroscopy. The fluorescence measurement preferably comprises individual cell fluorescence intensities and the mean fluorescence intensity (MFI).

Preferably, the probability density function of step (d) is selected from the group of functions consisting of lognormal, normal, Weibull and exponential. The probability function chosen will have some impact on the value of σ, and therefore will have some impact when determining the optimal concentration from plots of σ versus concentration. Most preferably, the probability density function is lognormal. However, the simulation of the surviving fraction can also directly employ the incorporation data (e.g. flow cytometry data) without relying on a lognormal or other function fit to obtain σ.

The probability function of the plot of surviving cell fraction versus the amount of incorporated therapeutic agent can be any typical dose-response function. Preferably this survival probability function is selected from the group of functions consisting of exponential and linear-quadratic, and is most preferably exponential.

Preferably, the Monte Carlo simulation method comprises flow-cytometry assisted Monte Carlo simulation.

A second embodiment of the invention is directed to a method for predicting the response of an individual patient's cancer cells to therapeutic intervention comprising the steps of:
  (a) exposing populations of said cancer cells to increasing concentrations of a candidate therapeutic agent for said cancer;
  (b) measuring by fluorescence spectroscopy the incorporation of said therapeutic agent in said populations on a cell-by-cell basis using a flow cytometer, to provide net mean fluorescence intensity (MFI);
  (c) plotting the number of cells versus the net MFI, to obtain a distribution plot for said population;
  (d) fitting said distribution plot to a lognormal probability density function to obtain a lognormal distribution curve and the standard deviation, σ, for each population; and
  (e) identifying the optimal concentration of said therapeutic agent for said cancer patient from changes in slope of a plot of σ as a function of concentration of said therapeutic agent.

Preferably, the method further comprises the step of predicting the surviving fractions of said cell populations using a flow-cytometry assisted Monte Carlo simulation that accounts for the characteristics of said lognormal distribution curve.

In a further embodiment of the invention, the cancer cells are exposed to increasing concentrations of a plurality of therapeutic agents, and the optimal concentration of each drug/agent is identified, and the simulation results are used to identify a combination of therapeutic agents that affords a high degree of killing of the cancer cells. Preferably the degree of killing of the cancer cells is about 99% or greater, more preferably 99.9% or greater, and most preferably 99.99% or greater. The method can also be used to identify a combination of drugs that affords the optimum degree of killing of the cancer cells.

In yet another embodiment of the invention, the method further comprises the step of identifying one or more drugs that can be added to a combination of therapeutic agents to facilitate the killing of subpopulations of cells that would otherwise escape killing by said combination.

Yet another embodiment of the invention comprises a method of high-throughput drug discovery comprising the method described above for predicting the response of an individual patient's cells to therapeutic intervention. Such an embodiment can be implemented on a high-throughput drug discovery platform. For example, in one embodiment, a tissue sample from a patient would be cultured and loaded into a high-throughput drug discovery device which is coupled to a flow cytometer, numerous combinations from a library of drugs would be screened, and a cocktail specific for the patient at hand would be identified.

Still another embodiment of the invention is directed to a 2-stage targeting method of treating a disease or condition for a patient in need thereof, the method comprising:
  (1) identifying and providing a plurality of candidate targeting agents relevant to the disease or condition of said patient, wherein said targeting agents are two-stage agents comprising:
    (a) Stage 1 agents which are non-toxic and target the diseased or affected cells; and
    (b) Stage 2 agents which bind to said Stage 1 agents and carry at least one additional agent selected from the group consisting of toxins, radionuclides and fluorochromes, wherein each Stage 2 agent can only bind to a single corresponding Stage 1 agent;
  (2) injecting said patient with a cocktail of Stage 1 agents via a route appropriate to said disease or condition, and allowing sufficient time for maximum uptake by said diseased or affected cells and substantial clearance of unbound Stage 1 agents;
  (3) withdrawing a sample of said patient's diseased or affected cells loaded with Stage 1 agents;
  (4) treating said sample of said cells in vitro with a cocktail of said Stage 2 agents, wherein each Stage 2 agent carries a unique fluorochrome, and wherein said Stage 2 agents bind to said Stage 1 agents loaded into said cells;
  (5) quantifying the amount of each Stage 2 agent binding to each diseased or affected cell using fluorescence spectroscopy;
  (6) predicting the response of said diseased or affected cells for every possible combination of Stage 1 and Stage 2 agents using the above method for predicting the response of an individual patient's cells to account for the lognormal distribution of each agent, and identifying the optimal combination of said agents;
  (7) arming each Stage 2 agent of said optimal combination with one or more therapeutic agents selected from the group consisting of toxins, radionuclides, and combinations or two or more thereof, to form an armed cocktail;
  (8) optionally, repeating step (2); and
  (9) injecting said armed cocktail into said patient.

The method may further comprise repeating steps (3) through (6) with healthy cells of said patient in place of diseased/affected cells, in order to assess the uptake of said Stage 1 and Stage 2 agents in each healthy cell.

A further embodiment of the invention is directed to a computational method for processing the above-indicated data, including flow cytometry data, in order to determine the parameter σ and calculate therefrom the optimal dose, or effective dose, of each component of the drug cocktail.

In addition, the above-identified methods can be used in radioimmunochemotherapy to predict the toxicity of cocktails of α-emitting radiopharmaceuticals and chemotherapy drugs in a manner that takes into account the effects of lognormal and other nonuniform distributions of agents within cell populations. These agents can interact with one another and cause greater than expected effects based on their single-agent toxicities. The approach is employed advantageously in the selection of agents for the design of highly effective α-particle based therapeutic cocktails that are capable of targeting the diversity in tumor cell populations.

The above-identified methods have the capacity to predict clonogenic survival after multi-modality therapy, using flow cytometry-assisted Monte Carlo simulation. It is demonstrated herein that Monte Carlo simulation using cellular agent incorporation based on individual cell fluorescence intensities of therapeutic agents is a suitable predictor of cell survival. This model accounts for the lognormal distribution of cellular uptake of the agents, and is capable of predicting treatment response on a cell-by-cell basis.

Cellular Uptake of $^{210}$Po-Citrate, Daunomycin, and Doxorubicin

Figure 1C:
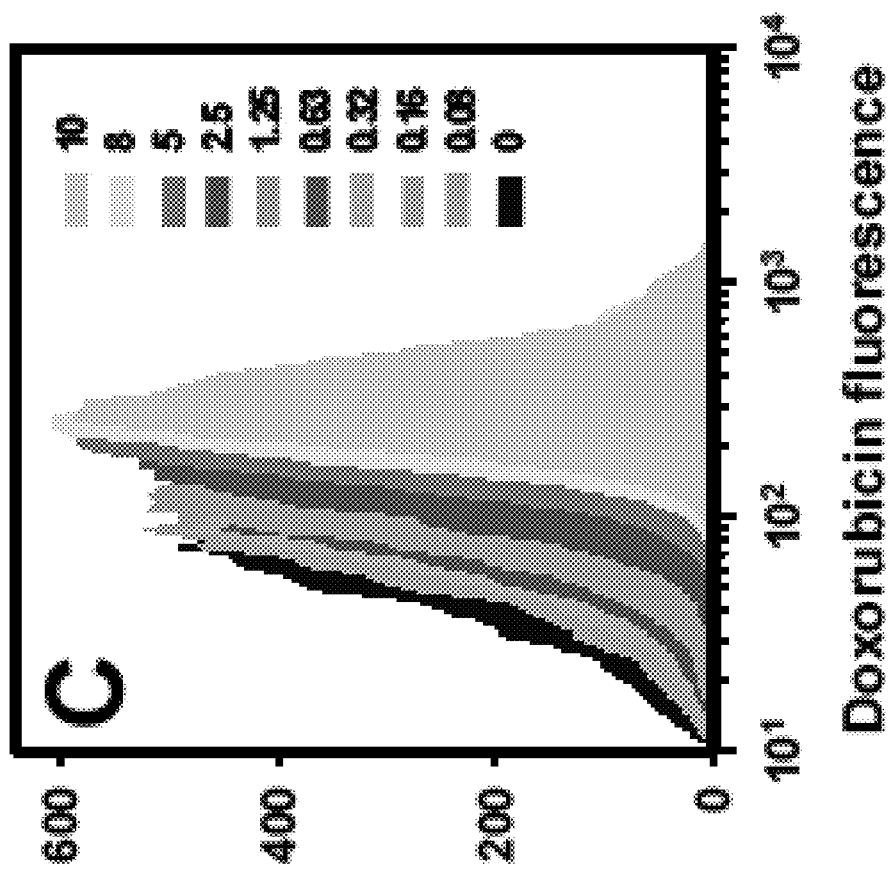
Figures 2A, 2B, 2C:
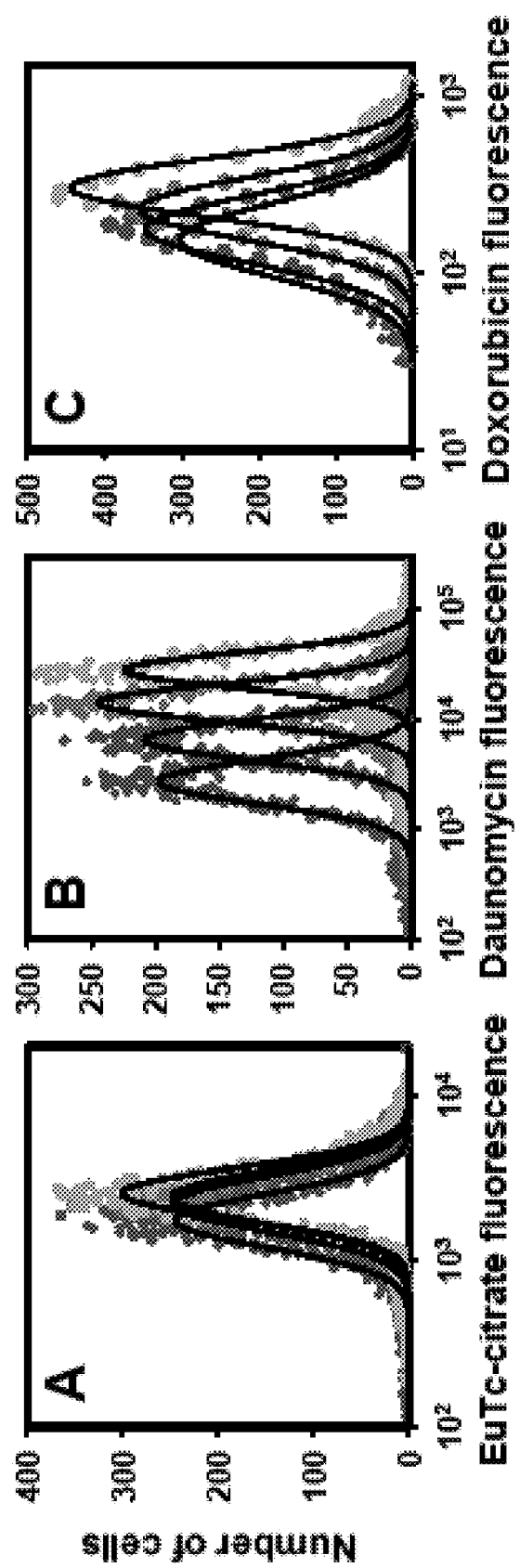
FIG. 2 shows the least squares fits of the flow cytometry fluorescence intensity histograms to a lognormal probability distribution. The histograms correspond to (A) EuTc-citrate, (B) daunomycin, and (C) doxorubicin.
Figures 3A, 3B, 3C:
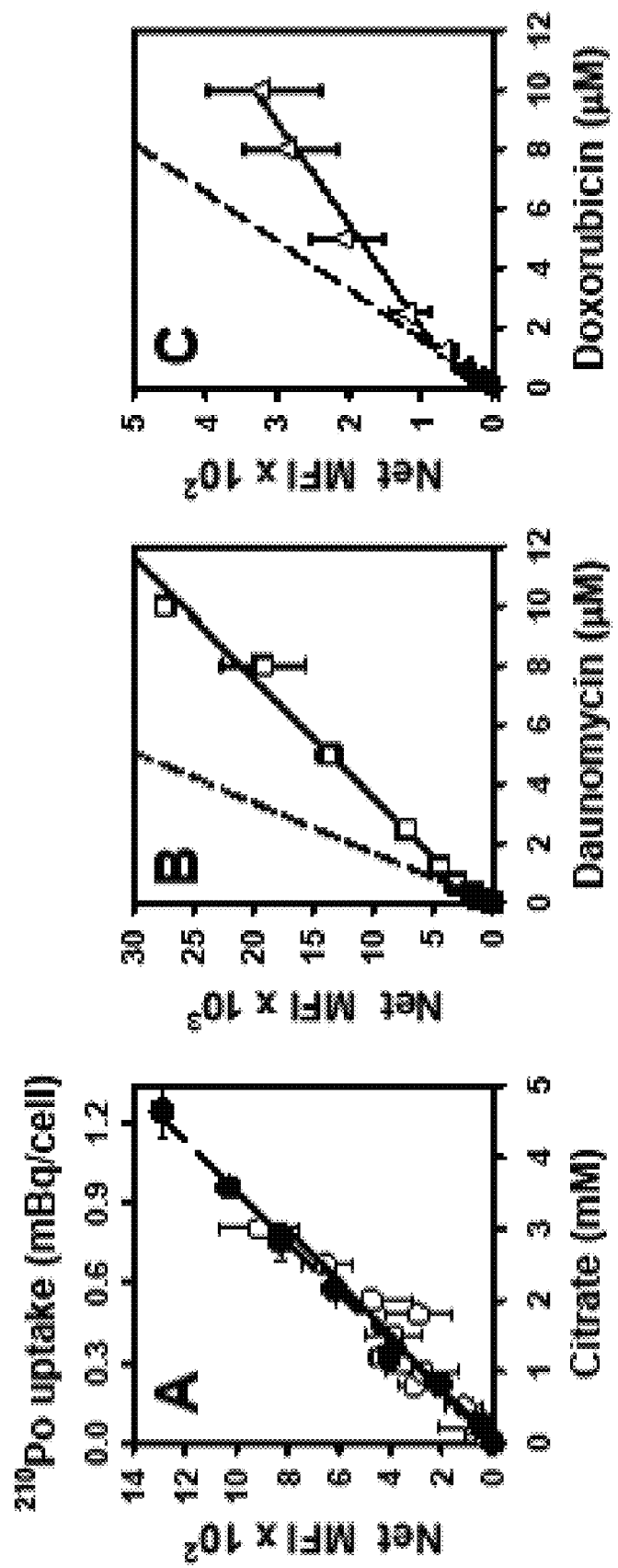
FIG. 3A displays net mean fluorescence intensity (MFI) of europium tetracycline-citrate complex (EuTc-citrate) as a function of extracellular citrate concentration (open circle, solid line) and corresponding mean $^{210}$Po activity per cell (filled circle, dashed line). Lines represent least squares fits of the data to linear functions: MFI=267±16 (mmol/L)$^{-1}$× $C_{cit}$, and MFI=1058±19 (mBq/cell)$^{-1}$×<$a_0$>, where $C_{cit}$ and <$a_0$> are the extracellular citrate concentration and mean cellular activity of $^{210}$Po, respectively. B displays net MFI of intracellular daunomycin after exposure to low extracellular concentrations (filled square, dashed line) and high concentrations (open square, solid line). Linear least squares fits to the data give MFI$_{dauno}$($C_{dauno}$<0.6 µmol/L)=5922 (µmol/L)$^{-1}$×$C_{dauno}$ and MFI$_{dauno}$ ($C_{dauno}$>0.6 µmol/L)= 2480 (µmol/L)$^{-1}$×$C_{dauno}$+1161. C. Net MFI of intracellular doxorubicin after exposure to low extracellular concentrations (filled triangle, dashed line) and high concentrations (open triangle, solid line). Linear least squares fits to the data give MFI$_{doxo}$ ($C_{doxo}$<1 µmol/L)=61 (µmol/L)$^{-1}$×$C_{doxo}$ and MFI$_{doxo}$($C_{doxo}$>1 µmol/L)=40 (µmol/L)$^{-1}$×$C_{doxo}$+29. For all cases, error bars represent standard error (SE) of three independent experiments.

FIG. 1 shows flow cytometry histograms of the fluorescence intensity of V79 cells that were treated with $^{210}$Po-citrate (FIG. 1A), daunomycin (FIG. 1B), or doxorubicin (FIG. 1C) at concentrations ranging from 0-3 mmol/L, 0-10 μmol/L, and 0-10 μmol/L, respectively. Note that the peaks shift toward higher mean fluorescence as the extracellular concentration of the drug increases. The relatively symmetric nature of the histograms as plotted on a linear-log scale is suggestive of a lognormal distribution of each agent among the cell population. Fluorescence intensity distribution is a lognormal function of the fluorescence intensity I, $$f(I) = \frac{g}{I\sigma\sqrt{2\pi}} e^{\frac{-(\ln I - \mu_I)^2}{2\sigma^2}}, I > 0$$

where $\mu_I$ is the scale parameter, σ is the shape parameter, and g is a constant. Least squares fits of the data to this distribution are shown in FIG. 2. Although not observed for EuTc-citrate (FIG. 2A), there is a decrease in the breadth of the lognormal distributions corresponding to daunomycin (FIG. 2B) and doxorubicin (FIG. 2C). Treatment with 0.1 mmol/L citrate resulted in a large increase in mean fluorescence intensity (MFI) from ~163 in untreated samples to ~2000. This can be attributed to the high sensitivity of EuTc for detecting citrate. EuTc is capable of detecting citrate in solutions at concentrations ~1000-fold lower. Since 0.1 mmol/L corresponded to an intracellular $^{210}$Po activity of ~0.02 mBq/cell, which translates to no significant cell kill, background fluorescence of 2000 units was subtracted from the MFI of each sample to obtain a net MFI. The net MFI was then plotted as a function of extracellular citrate concentration (FIG. 3A). With knowledge of the linear correlation between MFI and extracellular citrate concentration, and knowledge of the linear correlation between cellular uptake of $^{210}$Po and extracellular $^{210}$Po-citrate concentration, a similar correlation could be established between MFI and intracellular $^{210}$Po activity (FIG. 3A). A very strong correlation is apparent between cellular incorporation of the vehicle citrate and intracellular $^{210}$Po-activity. Similarly, the fluorescence histograms obtained after treatment of cells with daunomycin and doxorubicin are presented in FIGS. 3B and 3C, respectively. For both drugs, the MFI for the untreated controls were subtracted as background from the MFI of each sample, and the net MFI was plotted against extracellular drug concentration. In each case, net MFI was linearly correlated with drug concentration.

Briefly, flow cytometry was used to quantify their mean fluorescence intensity (MFI) per cell, <I>, as a function of the concentration of the agent in the cell culture medium. The net mean fluorescence intensities per cell, $<I>_{net}$, were determined by subtracting control autofluorescence $<I>_{control}$, Equation (1):

$$<I>_{net} = <I> - <I>_{control} \tag{1}$$

The surviving fraction SF of cells exposed to the agent was assessed with a clonogenic survival assay and plotted as a function of several different variables including extracellular concentration, $<I>_{net}$, absorbed dose (Gy), and mean cellular activity (mBq/cell). The resulting survival curves were of a 1- or 2-component exponential form. Analogous to the cellular activity and absorbed dose required to achieve 37% survival, $a_{37}$ and $D_{37}$, the net mean lethal fluorescence intensity of the drug required to achieve 37% survival, $<I>_{net,37}$, can be defined similarly and obtained from plots of SF versus $<I>_{net}$.

Cellular Dosimetry

The absorbed dose to the cell nucleus was determined as known in the art. Since cells were treated with $^{210}$Po-citrate as a single-cell suspension and were subsequently seeded for colony formation, the small contribution of cross-irradiation from neighboring cells in the colony can be ignored because it is essentially counterbalanced by the reduction in self-dose caused by flattening of cells during the colony forming period. The data was least squares fitted to obtain a mean biologic half-time of 11.6 h. Considering the physical half-life of 138 d for $^{210}$Po, this yields an effective half-time $T_e$ of 11.6 h. This $T_e$, the maintenance period of 2.5 h, the subcellular distribution of $^{210}$Po-citrate (28% nucleus, 72% cytoplasm) for V79 cells and published S values, were used to calculate a mean absorbed dose to the cell nucleus of 5.8 Gy/mBq of $^{210}$Po incorporated into the cell.

Toxicity of $^{210}$Po-Citrate, Daunomycin, and Doxorubicin

Figures 4A, 4B, 4C:
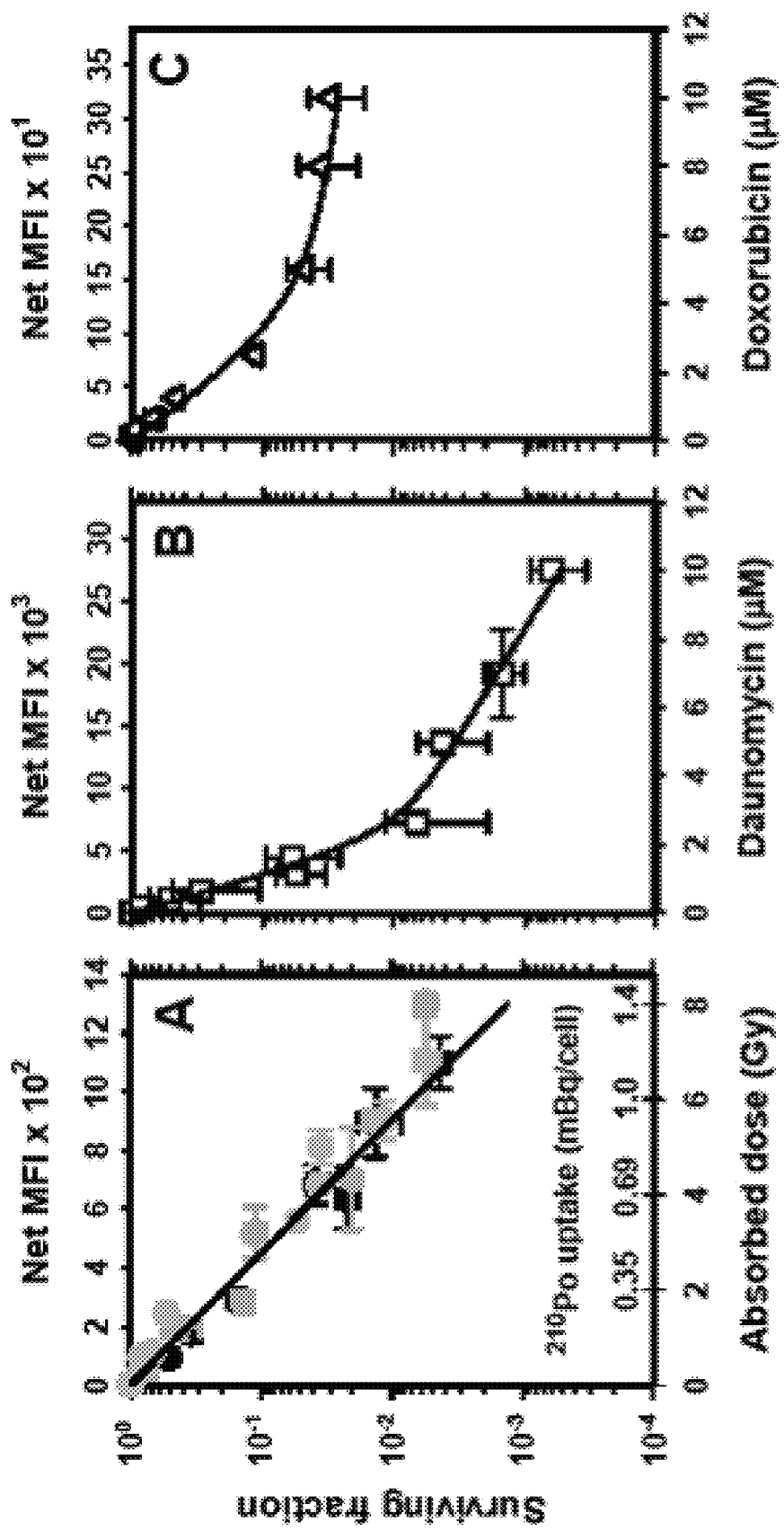
FIG. 4 shows the surviving fraction (SF) of V79 cells after treatment with various agents. A displays $^{210}$Po-citrate for three independent experiments, SF plotted against absorbed dose to the cell nucleus, intracellular $^{210}$Po activity, and net mean fluorescence intensity (MFI) of the europium tetracycline-citrate complex. Data plotted are from three independent experiments. Curve represents a least squares fit of the data to a single component exponential function. B displays daunomycin (open square), SF plotted against extracellular drug concentration and against net MFI of the drug. C displays doxorubicin (open triangle), SF plotted against extracellular drug concentration and against net MFI of the drug. Curves for daunomycin and doxorubicin represent least-squares fits to a two-component exponential function. For $^{210}$Po-citrate, horizontal and vertical error bars represent SE of mean cellular activity and surviving fraction of triplicate measurements, respectively. For daunomycin and doxorubicin, horizontal and vertical error bars represent SE of Net MFI and surviving fraction for three independent experiments.

To evaluate $^{210}$Po cytotoxicity, the surviving fraction was plotted as a function of EuTc-citrate net MFI, mean cellular uptake of $^{210}$Po, and mean absorbed dose to the nucleus (FIG. 4A). The data indicate that net MFI of the vehicle (citrate) is a good predictor of $^{210}$Po toxicity within the range of cellular activities employed. The relationships between cell survival and EuTc-citrate net MFI or cellular $^{210}$Po activity can be described by an exponential function SF=exp($-A/A_1$). The relationship between cell survival and drug net MFI (or extracellular concentration) for daunomycin and doxorubicin are illustrated in FIGS. 4B and 4C, respectively. For both drugs, clonogenic survival and cellular drug uptake (as determined by net MFI) are related via two component exponential functions SF=b exp($-A/A_1$)+(1-b)exp($-A/A_2$). A is the intracellular activity of $^{210}$Po-citrate, absorbed dose to the cell nucleus, or drug concentration. Least squares fits of the survival data to this function were performed. The variable b is a fitted parameter.

Role of Agent Distribution in Cellular Toxicity

To evaluate the role of the distribution of $^{210}$Po-citrate, daunomycin, and doxorubicin within a cell population in their subsequent toxicity, the fluorescence histograms presented in FIG. 1 were fitted to the lognormal probability density function to obtain the shape parameter a (FIGS. 1 and 2). Although increasing intracellular $^{210}$Po activity did not have an appreciable effect on σ over the entire range of concentrations studied for $^{210}$Po-citrate, increases in extracellular drug concentration had a marked impact on σ for both daunomycin and doxorubicin. The relationship between cell survival and σ for the three agents is illustrated in FIGS. 6 and 7. These plots show that σ for $^{210}$Po-citrate does not change appreciably as the surviving fraction decreases. However, σ for daunomycin and doxorubicin decreases substantially as the surviving fraction decreases.

It is now well established that chemotherapy drugs and radiopharmaceuticals are typically heterogeneously distributed in tissues at the macroscopic, cellular, and subcellular levels. In the case of radiopharmaceuticals, this complicates estimation of cellular absorbed doses based on cellular activities, and causes the relationship between incorporated radioactivity and biologic response to be complex. Several in vitro studies have demonstrated saturation in cell kill with increasing activity per cell following exposure to a variety of radiochemicals, and have attributed the phenomenon to the lognormal nature of the agent distribution. This has also been shown for two chemotherapeutics, daunomycin and doxorubicin. Given the difficulty that is being experienced clinically in terms of sterilizing tumor cell populations with these and other agents, a more thorough understanding of their lognormal distributions and how they affect cell killing is needed to assist in selecting combinations of agents and guide the dosing of the constituent agents. Some enlightenment can be obtained by interpreting the flow cytometric and clonogenic survival studies described above. FIG. 1 demonstrates that flow cytometry can, under certain circumstances, be used to quantitate intracellular drug concentration. In the present case, this approach is used for EuTc-citrate (surrogate for $^{210}$Po-citrate), and two different chemotherapy drugs, daunomycin and doxorubicin. The distributions of intracellular agent concentration are lognormal (FIG. 2). As shown in FIG. 2A and FIG. 1, the EuTc-citrate is exquisitely lognormal throughout the range of extracellular drug concentrations studied. Not only is it lognormal, but the breadth of the peak remains consistent as well. This fact is confirmed by the absence of change in σ that is observed for EuTc-citrate in FIGS. 6 and 7. In contrast, the breadths of the peaks and their corresponding σ values change markedly for daunomycin and doxorubicin (FIG. 7). Furthermore, there are notable exceptions to the lognormality of the data acquired for daunomycin and doxorubicin (FIG. 1). In the case of daunomycin, there appears to be a growing population of cells on the low fluorescence side of the peak as the extracellular concentration increases. Conversely, doxorubicin's small departure from lognormality occurs at low extracellular drug concentrations. These changes occur in concert with changes in the slope of the drug uptake versus concentration of the drug in the extracellular medium, as emphasized by the dashed versus solid lines in FIGS. 3B and 3C. The net MFI of intracellular EuTc-citrate is strongly correlated with both extracellular citrate concentration and intracellular $^{210}$Po activity (FIG. 3A), indicating that MFI of EuTc-citrate is related to $^{210}$Po toxicity. Similarly, the data for daunomycin and doxorubicin in FIGS. 3B-C support the notion that the extent of agent incorporation by cells can be used as a predictor of their cytotoxicity. To validate the latter, cell survival is plotted against net MFI and extracellular drug concentration, or against intracellular $^{210}$Po activity and absorbed dose to the cell nucleus from $^{210}$Po-citrate (FIG. 4A). For $^{210}$Po-citrate, less than 2-logs of cell killing is observed. The relationship between the surviving fraction and net MFI (or cellular activity or absorbed dose) is exponential. Notably, neither the slope of the cellular uptake curve (FIG. 3A), nor the slope of the survival curve (FIG. 4A), nor the value of the shape parameter (FIGS. 6 and 7), change over the course of the concentrations required to achieve zero to two logs of cell kill. These conditions may be requirements needed to achieve a monoexponential survival curve and avert tailing of the survival curve. The data in FIGS. 4B-C illustrate that cell survival is related to extracellular concentration (or net MFI) of daunomycin and doxorubicin by a 2-component exponential function, with tails analogous to those observed using radiochemicals. Daunomycin and doxorubicin are closely related anthracyclines and interact with DNA by intercalation. Based on extracellular drug concentration in V79 cell cultures, daunomycin ultimately emerged to be more cytotoxic than doxorubicin. While this may be due to differences in the extent to which the drugs are incorporated, this cannot be ascertained by flow cytometry alone but rather with the help of cellular uptake studies with daunomycin and doxorubicin labeled with $^3$H or $^{14}$C at known specific activities. What is certain is that the slope of the cellular uptake curves (FIGS. 3B-C), and the slope of the survival curves (FIGS. 4B-C), and the value of the shape parameter (FIG. 7), all changed over the span of concentrations required to see the emergence of a tail in the survival curves. The presence of these conditions appears to be related to the two-component exponential survival curves. In fact, the concentration (ca. 1-2 μmol/L) at which these parameters begin to change (FIGS. 2, 3, 6 and 7) appears to coincide with the transition to the second component (FIG. 4).

The mean lethal concentrations for daunomycin and doxorubicin are 0.24 and 1.26 μmol/L, respectively. This indicates that low extracellular concentrations of daunomycin are ~5× more lethal than doxorubicin in V79 cells. The mean lethal absorbed dose for $^{210}$Po-citrate is 1.2 Gy. This arises from an uptake of 0.21 mBq/cell which corresponds to about 3600 atoms of $^{210}$Po. Although the survival curve is similar to that obtained previously, the present mean lethal dose is higher than the former value of 0.7 Gy. This is largely due to improved S values. Although, there is an interest in using multimodal approaches that involve the concomitant delivery of chemotherapeutic and radiotherapeutic agents for cancer treatment, the efforts have mostly not been directed at using agent-specific distribution profiles to target all malignant cells. To facilitate the design of cocktails that effectively target all cells of interest, an in-depth knowledge of the distribution profile of each agent is required. This warrants the ability to express cellular incorporation of agents in absolute units on a cell-by-cell basis. As an initial step towards this end, the flow cytometric histograms presented in FIG. 2 were fitted to the lognormal probability density function, and the derived shape parameters (σ) were plotted against intracellular $^{210}$Po activity or extracellular drug concentration. It is not surprising that these data are closely analogous to the established relationship between heterogeneity of intracellular incorporation of doxorubicin and extracellular drug concentration, as the shape parameter is a measure of the broadness of a distribution profile. While a small σ implies a narrow distribution profile (i.e. σ→0) when all cells incorporate the same amount of agent), a large σ signifies a wide spread in distribution. In practice, σ>0 and therefore subpopulations of cells will always incorporate subtoxic amounts of any given agent. However, as it has been shown as part of the present invention, the value of σ is not itself necessarily the primary determinant of the shape of the survival curve. Rather, changes in the value of σ (FIG. 7) and changes in the slope of the cellular uptake curves (FIGS. 3B and 3C), appear to correlate with changes in the transition from the first component to second component of the two-component exponential survival curves (FIGS. 4B and 4C). Hence, formulation of recipes for combined modality therapy should seek to use flow cytometry distribution information to identify the drug concentration that will achieve the first component of killing. A similarly optimized additional agent could then be added with the aim of targeting cells that had low uptake of the first drug. Successively adding additional drugs would ultimately seek to achieve a net heterogeneity of σ→0, based on incorporation of all agents. It should be noted that findings related to the distribution of therapeutic agents among a population of cells, and their corresponding dose response characteristics, may vary considerably depending on cell type and the microenviroment within which the cells reside. In addition, factors such as resistant subpopulations can have a significant impact on the shape of the response curve. Therefore, caution is needed when cocktails are formulated based on in vitro findings and then extrapolated to the in vivo setting encountered in the clinic.

The present invention demonstrates that the distribution of cellular radioactivity within a cell population is adequately described by a lognormal probability density function. The ubiquitousness of the lognormal distribution has been further demonstrated by the cellular uptake profiles of two different chemotherapeutic drugs. Changes in the value of the lognormal shape parameter and changes in the slope of the cellular uptake curves with increasing drug concentration flag the onset of saturation in the dose response curve. Accordingly, measurement of these changes using flow cytometry, or another analytical technique, preferably a high-speed technique, can be employed to rapidly predict biological response to the drug, and ultimately to formulate a highly effective therapeutic cocktail.

Cocktails of Therapeutic Agents

One multiple-therapeutic agent embodiment of the present invention involves a cocktail of radioimmunotherapy and chemotherapy agents. Informed radioimmunotherapy/chemotherapy is one option for front-line defense against metastatic and residual disease in adjuvant external beam radiotherapy and surgery. However, one major limitation has been the difficulty in relating cellular incorporation of therapeutic agents, on a cell-by-cell basis, to resulting biological effects. The models for predicting the distribution of cytotoxic agents among a cell population, at the single-cell level, as disclosed above, now also provide a cocktail approach whereby all malignant cells can be effectively targeted. This flow cytometry-based approach, taking explicit account of the lognormal distribution of cellular uptake of the agents, enables prediction of treatment response on a cell-by-cell basis, and has now been shown to be invaluable in the selection of agents for the design of highly effective therapeutic cocktails that are capable of targeting the diversity in tumor cell populations. Further, such cocktails can be created not only for treatment of cancer, but also for infectious diseases, and other diseases that are amenable to targeted therapies. Furthermore, this single-cell Monte Carlo technique can be used to resolve difficulties encountered when attempting to predict biological response at the multicellular level using macroscopic mean agent doses.

Over the past two decades, interest in the use of α-emitting radionuclides in radioimmunotherapy has grown significantly. However, a major unresolved concern is that the toxicity of α-emitting radionuclides does not allow administration of high activities. As such, targeting procedures would need to be optimized to minimize normal tissue toxicity. This can be achieved via multi-modality radioimmunotherapy, which employs combinations of radioimmunotherapy and chemotherapy. Multi-modality radioimmunotherapy approaches seek not only to effectively target all malignant cells, but also to significantly reduce the amount of each constituent of the cocktail. To guide design of effective cocktails of α-emitting radiopharmaceuticals and chemotherapy drugs, there is the need to assess the role of nonuniform agent distribution on modification of α-particle radiotoxicity by chemotherapy drugs. Furthermore, the capacity to predict such modifications in treatment response on a cell-by-cell basis should greatly improve treatment outcomes through individualized staging prior to therapy.

As has now been demonstrated, concomitant treatment of Chinese hamster V79 cells with an α-emitting radiochemical, $^{210}$Po-citrate, and either daunomycin or doxorubicin, resulted in an enhancement of α-particle radiotoxicity. Further, the toxicity of the combination treatment can be predicted with a Monte Carlo simulation approach based only on knowledge of the initial slope of the cell survival curves of the individual agents and information on the distribution of agent incorporation among cell populations.

Examples

Predicting Cell Survival Based on Flow Cytometry Gating

Three approaches to modeling the surviving fraction of cells were undertaken. In the first approach, flow-cytometry fluorescence histograms of agent uptake were prepared and the cells were gated relative to control autofluorescence using FlowJo® software (TreeStar). The fractions of agent-negative cells were defined as the proportions of fluorescence spectra that had intensities below the maximum intensities of control samples (i.e. the fraction of fluorescence spectra below maximum autofluorescence). For $^{210}$Po, 0.1 mM citrate which corresponded to a nontoxic cellular activity of 0.03 mBq/cell was used for autofluorescence. In this simple approach, the gated subpopulations of agent-negative cells were considered as survivors, whereas gated subpopulations of agent-positive cells were considered dead. The surviving fraction was taken as the number of agent-negative divided by the sum of agent-negative and agent-positive cells.

Figure 5:
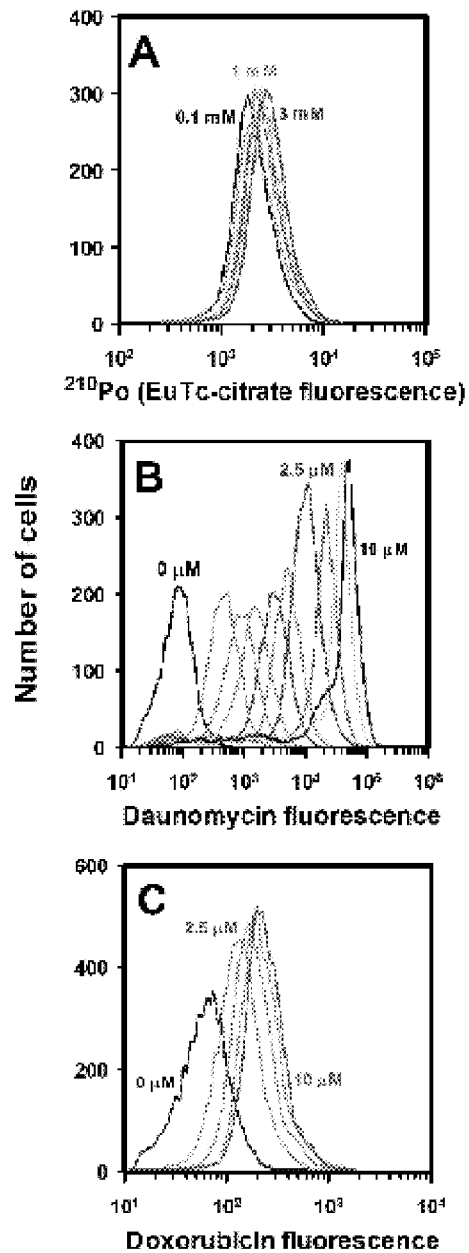
FIG. 5 shows a flow chart of the Monte Carlo procedure for determining fraction of surviving cells based on cellular fluorescence intensity profiles of the incorporated agent. In STEP 1, flow cytometry was used to obtain fluorescence intensity of EuTc-citrate ($^{210}$Po-citrate), daunomycin, and doxorubicin in individual V79 cells in a suspension culture. The distribution of measured cellular fluorescence intensities, adapted from FIG. 1, is shown in (A) 0.1-3 mM citrate, (B) 0-10 µM daunomycin, or (C) 0-10 µM doxorubicin. After calculating the probability of survival $P_i(I_i')$ for the $i^{th}$ cell based on the normalized fluorescence intensity $I_i'$ (STEP 2), a random number RAND$_i$ (0<RAND$_i$≤1) was generated as depicted in STEP 3 by the dice. If RAND$_i$<$P_i(I_i')$, then the cell was scored as a survivor, otherwise it was considered dead (STEP 4). A surviving cell is represented by a blossoming tree with leaves, while a dead cell is depicted by a tree without leaves. By repeating STEPS 1-4 for every cell in each population, the surviving fraction for any sample population was calculated as illustrated in STEP 5.

Predicting Cell Survival Based on Monte Carlo Analysis of Cellular Fluorescence Intensity The second approach, depicted in FIG. 5, employs a Monte Carlo simulation that uses experimental individual cell fluorescence intensities $I_i$ for the agent under consideration. The flow cytometry data for citrate, daunomycin, and doxorubicin, consisting of fluorescence intensities emitted by individual cells in a population after incorporation of a fluorescent agent ($I_1, I_2, I_3, \ldots, I_i$), were exported into Microsoft Excel (Redmond, Wash.) spreadsheets. These raw values were normalized to $<I>_{net}$ as per Equation (2).

$$I'_i = I_i \left( \frac{\langle I \rangle_{net}}{\langle I \rangle} \right), \quad (2)$$

where $$\langle I \rangle = \frac{1}{N} \sum_{i=1}^{N} I_i,$$

and N is the number of cells analyzed. The cytotoxicity of a therapeutic agent in a given cell is assumed to be exponentially related to the cellular uptake of the agent, Exponential functions are widely used to model the probability of cell death following cytotoxic insults from ionizing radiation and chemicals. Accordingly, the survival probability $P_i$ of the $i^{th}$ cell with normalized fluorescence intensity, $I_i'$, may be expressed as:

$$P_i(I'_i) = e^{-\frac{I'_i}{\langle I \rangle_{net,37}}}. \quad (3)$$

The resulting probability for each cell was compared with a random number generated from a uniform probability distribution by Excel, 0<$RAND_i$≤1, and a binary value was assigned to the survival $s_i$ of the $i^{th}$ cell:

$$s_i = \begin{cases} 0 & \text{dead cell} \quad RAND_i > P_i(I'_i) \\ 1 & \text{live cell} \quad RAND_i \leq P_i(I'_i) \end{cases} \quad (4)$$

A new random number was generated for each cell. This type of random number approach to determining the fate of each cell was also used in our recent communication (Rajon et al. 2011). Therefore, the surviving fraction of a population of N cells treated with a given concentration of an agent that yields net mean fluorescence intensity per cell, $\langle I \rangle_{net}$, may be expressed as:

$$SF(\langle I \rangle_{net}) = \frac{1}{N}\left(\sum_{i=1}^{N} s_i\right) \quad (5)$$

Care must be exercised when $$\sum_{i=1}^{N} s_i$$

is small because the statistical uncertainty of the Monte Carlo calculation of SF is high under such circumstances. This occurs at high agent concentrations that cause low surviving fractions. This is best circumvented by analyzing a larger number of cells. A less preferable alternative is to run additional simulations with new random number sequences and average the results.

Predicting Cell Survival Based on Mean Cellular Uptake

The third approach uses the same Monte Carlo approach for determining the fate of each cell, however, it is assumed that every cell in the population contains the same amount of drug. That is, each cell is assigned a fixed net mean fluorescence $\langle I \rangle_{net}$ which in essence corresponds to case wherein the lognormal shape parameter σ→0. In this instance, the probability of survival of the $i^{th}$ cell is given by $$P_i(\langle I \rangle_{net}) = e^{\frac{\langle I \rangle_{net}}{\langle I \rangle_{net,37}}} \quad (6)$$

The surviving fraction of the population is obtained using the same Monte Carlo method described above except that Equation (6) was used instead of Equation (3) to calculate the probability of survival.

Materials and Methods
Cell Line and Monolayer Culture

Chinese hamster V79 lung fibroblasts were used. Two different formulations of minimum essential media (MEMA and MEMB) were used, as known in the literature. All media and supplements were Gibco (Carlsbad, Calif.), including fetal calf serum (catalog no. 10437, lot no. 539574). For routine maintenance, cells were grown as monolayers in Falcon 25-cm² tissue culture flasks (BD, Franklin Lakes, N.J., catalog no. 353082) at 37° C., 5% $CO_2$-95% air, and subcultured twice weekly. For experiments, V79 cells (passage 4-11) were transferred into Falcon 225-cm² flasks (BD, catalog no. 353138), and were used upon reaching 80%-90% confluence.

Suspension Cell Culture

Cells grown in 225-cm² flasks were trypsinized (0.25% trypsin, Gibco, catalog no. 25200-056), and MEMB was added to obtain 2×10⁶ cells/mL. Aliquots of 1 mL were placed in Falcon 17×100 mm polypropylene tubes (BD, catalog no. 352018) and placed on a rocker-roller (Thermo Fisher, Fair Lawn, N.J.) for 3 hours at 37° C. with 5% $CO_2$ and 95% air. After this conditioning period, cells were treated with drug or radiochemical. Cell cultures were exposed to radiochemical and drugs for 0.5 and 2.5 h, respectively.

Cellular Incorporation of $^{210}$Po-Citrate, Daunomycin, and Doxorubicin $^{210}$Po-Citrate. The uptake of $^{210}$Po-citrate was determined on a cell-by-cell basis by flow cytometric techniques, using $^{210}$Po-free citrate. Briefly, V79 cells (2×10⁶ cells/mL) were treated with 0-3 mmol/L of citrate and incubated on a rocker-roller as described earlier. Cellular uptake of citrate was tracked using an europium tetracycline (EuTc) conjugate. Samples were washed 2× with 10 mmol/L MOPS buffer (Sigma, St. Louis, catalog no. M3183), after a 30 min exposure to citrate. The cells were resuspended in 1 mL of MOPS buffer containing EuTc (Sigma, catalog nos. 203254 for Eu and T7660 for Tc), transferred into 7 ml polystyrene flow cytometry tubes (BD, catalog no. 352054), and were incubated at room temperature (~22° C.) in the dark for 30 min. The final concentration of EuTc was 100 μmol/L. EuTc forms a ternary complex with citrate (EuTc-citrate) which is excitable at 488 nm, and its emission can be captured within the wavelengths transmitted by the 610/20 filter. After washing 2× with MOPS buffer, the samples were resuspended in 1 mL of MOPS buffer, passed 5× through a 21-gauge needle, and were analyzed by flow cytometry using an LSR II flow cytometer (BD), equipped with a 488 nm laser. Cellular incorporation of citrate, expressed in terms of the fluorescence intensity per cell or mean fluorescence intensity (MFI) of EuTc-citrate, was used as a surrogate measure cellular uptake of $^{210}$Po-citrate.

Daunomycin and Doxorubicin.

To determine the cellular uptake of daunomycin and doxorubicin, the cells were treated with 0-10 μmol/L of each drug in MEMB and incubated on a rocker-roller for 2.5 h. The cells were washed 2× with phosphate buffered saline (PBS), resuspended in 1 mL of PBS, passed 5× through a needle, and were immediately subjected to flow cytometric analysis. The 488 nm laser was used to excite intracellular daunomycin and doxorubicin, and the emission spectra were captured within the wavelengths transmitted by the 575/26 and 530/30 filters, respectively. Cellular incorporation of drugs was also expressed as MFI.

Toxicity of $^{210}$Po-Citrate $^{210}$PoCl₄ in 2 mol/L HCl was obtained at 370 MBq/mL from Eckert&Ziegler Isotope Products (Valencia, Calif., catalog no. 6310). $^{210}$Po-citrate was prepared as follows. Briefly, PoCl₄ solution was mixed with 1 mol/L sodium citrate in the ratio of 1:7 (final pH 5.8), and was diluted with MEMB to a volume of 4 mL (final pH 6.9). One milliliter of MEMB containing $^{210}$Po-citrate was added to the 1 mL of conditioned V79 cultures (2×10⁶ cells/mL), to arrive at a concentration of 0-250 kBq/mL (pH 6.9-7.0). After incubating for 30 min, the cells were washed 2× with MEMB, resuspended in 2 mL of MEMB, and incubated on a rocker-roller for 2.5 h to simulate concomitant drug exposure. The cells were resuspended in a 5 mL of MEMB, passed 5× through a needle, and counted with a Beckman Coulter Model Z2 (Brea, Calif.). Aliquots (500 µL) of the cell suspension were transferred to vials, mixed with 5 mL Ecolume (MP Biomedical, Solon, Ohio, catalog no. 882470), and counted with a Beckman Coulter LS6500, and the mean activity per cell was determined (efficiency, 50% as per prior studies). Aliquots of about $5\times10^5$ cells were counted in triplicate for $^{210}$Po activity and the cpm ranged from $10^3$-$10^5$. The triplicate measurements kept statistical variations to a minimum. Each sample was serially diluted and plated in Falcon 60×15 mm tissue culture dishes for colony formation. Cultures were incubated for 7 days, and the colonies were fixed in 95% ethanol, stained with 0.01% Amido Black, washed in tap-water, air-dried, and counted.

Biologic Clearance of $^{210}$Po

To determine the biologic clearance of $^{210}$Po from the cells, $4\times10^6$ cells/mL were treated with $^{210}$Pocitrate as described above. After two washes with MEMB, the cells were resuspended in 5 mL of MEMB, passed 5× through a needle, and Coulter counted. Aliquots of 500 µL of cells were transferred to vials and mixed with Ecolume. The remaining cell suspension was plated into 25-cm² flasks (1.0, 0.5, 0.5, 0.2 and $0.2\times10^6$ cells/flask). The cultures were harvested after 24, 48, 72, and 96 h, respectively. Each sample was processed for cell counting and liquid scintillation counting as described. All vials were counted after the last harvest. The ratio of cellular activity at each time point to that immediately after treatment was calculated and plotted.

Toxicity of Daunomycin and Doxorubicin

After conditioning, the cell cultures were treated with daunomycin (Sigma, catalog no. D8809) or doxorubicin (Sigma, catalog no. 44583) to a final concentration of 0-10 µmol/L in MEMB. The tubes were returned to the rocker-roller for 2.5 h. The cells were then processed for colony formation as described above.

Analysis of the Flow Cytometry Data for Cocktails of Agents

Samples.

Flow cytometry control samples consisted of cells treated with the following agents: 1) untreated, 2) 3 mM citrate, 3) 0.63 µM daunomycin, and 4) 2.50 µM doxorubicin, Daunomycin+citrate test samples were 0.63 µM daunomycin+0.1, 0.2, 0.5, 1.0, 1.5, 2.0, 2.5, or 3.0 mM citrate. Doxorubicin+citrate test samples were 2.50 µM doxorubicin+0.1, 0.2, 0.5, 1.0, 1.5, 2.0, 2.5, or 3.0 mM citrate.

Acquisition.

Fluorescence intensity histograms were acquired for each sample using an LSR II flow cytometer (BD). The europium tetracycline-citrate complex, daunomycin, and doxorubicin were excited with a 488 nm laser, and their emission spectra were captured within the wavelengths transmitted by the 610/20, 575/26 and 530/30 filters, respectively.

Analysis.

FlowJo software (TreeStar) was used to analyze each sample. Dot plots of forward scatter versus side scatter were created to gate cells from debris. Fluorescence intensities were compensated for overlapping emission spectra.

Results

Predicting Cell Survival Based on Flow Cytometry Gating

Cells with fluorescence intensities greater than the maximum autofluorescence were considered as agent-positive, while those with lower intensities were agent-negative. For $^{210}$Po-citrate and doxorubicin, most cells emerged as agent-negative regardless of agent concentration. This occurred because of the relatively small increase in $\langle I \rangle$ with increasing extracellular concentration of the agent. The proportion of daunomycin-positive cells consistently increased with increasing drug concentration. Conversely, the proportion of daunomycin-negative cells decreased substantially with increasing drug concentration. When surviving fraction, defined in this instance as fraction of agent-negative cells, was plotted as a function of agent concentration, it was apparent that agent-negativity, based on what might be considered conventional flow-cytometry gating, is not necessarily indicative of the ability of a cell to survive. For $^{210}$Po and doxorubicin, the fraction of agent-negative cells was found to significantly overestimate cell survival over the entire range of agent concentrations assessed. While there was relatively good agreement between daunomycin-negativity and clonogenic cell survival at low concentrations, the fraction of cells that were apparently drug negative failed to accurately predict survival at higher drug concentrations.

Predicting Cell Survival Based on Monte Carlo Analysis of Cellular Fluorescence Intensity To assess the capacity of Monte Carlo simulation of cell death and survival from cellular fluorescence data acquired by flow cytometry, the procedure depicted in FIG. 5 was employed. Only the net mean lethal fluorescence intensity, $\langle I \rangle_{net,37}$ and the measured fluorescence intensity in each cell of the treated population were needed to theoretically model the surviving fraction following treatment by each drug. Panels A, B and C of FIG. 5 show the lognormal nature of the distribution of measured fluorescence intensities following treatment with graded concentrations each drug. Application of Equation (3) to the two cell populations provides the survival probabilities $P_i(I_i')$ of each cell in populations treated with 0 or 5 µM daunomycin. By generating a random number $RAND_i$ between 0 and 1 (FIG. 5, STEP 3), and comparing it with the survival probability $P_i(I_i')$, the fate ($s_i$) of each cell was determined according to Equation (4) (FIG. 5, STEP 4). The surviving fraction of cells, $SF(\langle I \rangle_{net})$, based on normalized individual fluorescence intensities $I_i'$, were then calculated using Equation (5) (FIG. 5, STEP 5). There is a transition from nearly all live cells to nearly all dead cells as the agent concentration is increased.

The process described above for determining the surviving fraction $SF(\langle I \rangle_{net})$ was carried out for each of the cell populations which were treated with 0.1-3 mM citrate. The resulting theoretically modeled surviving fractions $SF(\langle I \rangle_{net})$ are plotted in FIG. 6A for $^{210}$P-citrate, along with the experimental clonogenic survival data. This process was repeated for daunomycin and doxorubicin to create the theoretical data points in FIGS. 6B and 6C, respectively. The Monte Carlo simulated cell survival is in good agreement with colony forming ability of V79 cells after treatment with the cytotoxic agents.

Predicting Cell Survival Based on Mean Cellular Uptake

Survival curves based on Monte Carlo analysis wherein each cell in the population contains the same amount of drug are presented as straight, dashed lines in FIG. 6. These provide an important point of comparison with the flow cytometry gating model and the Monte Carlo model that accounts for the lognormal distribution of cellular uptake of the agent.

Prediction of Multiple Agent Toxicity

The approach for modeling cell survival using a Monte Carlo simulation is based on individual cell fluorescence intensities $I_i$ for a single agent as described above. When cells were concomitantly treated with multiple agents, the fluorescence intensities of all agents within each cell of each treated population were measured simultaneously using flow cytometry. These data were used to perform a Monte Carlo analysis to simulate the surviving fraction of cells after treatment with all possible combinations of the agents. This process is depicted for a cocktail of agents in FIG. 8.

Flow cytometry of a population of N cells treated with a cocktail of agents provided the fluorescence intensity of each agent in each cell. These data were exported into Microsoft Excel (Redmond, Wash.) spreadsheets. The raw fluorescence intensities for the $j^{th}$ agent in the $i^{th}$ cell, $I_{ij}$, were normalized to $<I_j>_{net}$ for each agent as per Equation (2A)

$$I'_{ij} = I_{ij}\left(\frac{\langle I_j \rangle_{net}}{\langle I_j \rangle}\right), \tag{2A}$$

where $$\langle I_j \rangle = \frac{1}{N}\sum_{i=1}^{N} I_{ij},$$

and $<I_j>_{net}$ denotes the net mean fluorescence intensity per cell following exposure to the $j^{th}$ agent. $<I_j>_{net}$ is determined by subtracting the mean control autofluorescence, $<I_j>_{control}$, from the mean fluorescence intensity per cell in a treated population as defined by Equation (1A):

$$<I_j>_{net} = <I_j> - <I_j>_{control} \tag{1A}$$

For $^{210}$Po-citrate, a citrate concentration of 0.1 mM, which was found to correspond to a nonlethal cellular activity of 0.03 mBq/cell, was used for control autofluorescence. The net mean cellular fluorescence intensity of Agent j that yields 37% survival is denoted $<I_j>_{net,37}$ [20]. To account for natural variations in $<I_j>_{net,37}$ from experiment to experiment, it is necessary to obtain an $<I_j'>_{37}$ for each experiment from a calibration of an experimentally determined surviving fraction. Assuming that the toxicity of the $j^{th}$ agent in a given cell population is exponentially related to the cellular uptake of the agent, the surviving fraction of such a population based on its net mean fluorescence intensity, $<I_j'>$, is:

$$SF_j = e^{-\langle I'_j \rangle / \langle I'_j \rangle_{37}} \tag{7}$$

For instance, using the net mean fluorescence intensity of a cell population corresponding to 10% cell survival, $$\langle I'_j \rangle_{37} = -\frac{\langle I'_j \rangle}{\ln(0.1)}.$$

At the single-cell level, the survival probability of the $i^{th}$ cell with normalized fluorescence intensity, $I_{ij}'$, may be expressed as (FIG. 8, STEP 2):

$$P_i(I_{ij}') = e^{-I'_{ij}/\langle I'_j \rangle_{37}} \tag{6A}$$

Therefore, the survival probabilities for the $i^{th}$ cell when treated with Agent 1 or Agent 2 are given by $P_i(I_{i1}') = e^{-I'_{i1}/\langle I'_1 \rangle_{37}}$ and $P_i(I_{i2}') = e^{-I'_{i2}/\langle I'_2 \rangle_{37}}$, respectively.

To model cell survival following treatment with a cocktail of two agents, we hypothesize that a cell may die due to Agents 1 and 2 working independently or interactively. The survival probability $P_i(I_{i1}', I_{i2}')$ of the $i^{th}$ cell is represented by:

$$P_i(I'_{i1}, I'_{i2}) = \Omega(I'_{i1}, I'_{i2}) P_i(I'_{i1}) P_i(I'_{i2}) \tag{8}$$

$$\Omega(I'_{i1}, I'_{i2}) = \begin{cases} 1 & \text{agents work independently} \\ P_i(I'_{i1})P_i(I'_{i2}) & \text{agents work interactively} \end{cases} \tag{8A}$$

where $\omega_i(I_{i1}', I_{i2}')$ is a term that accounts for the interaction of the two agents.

The probability calculated with Equations (8) and (8A) was then compared with a random number, $0 < RAND_i \le 1$ (FIG. 8, STEP 3), and a binary value was assigned to the survival $s_i$ of the $i^{th}$ cell:

$$s_i = \begin{cases} 0 & \text{dead cell} \quad RAND_i > P_i(I'_{i1}, I'_{i2}) \\ 1 & \text{live cell} \quad RAND_i \le P_i(I'_{i1}, I'_{i2}) \end{cases} \tag{4A}$$

A new random number was generated for each cell. This approach to determining the fate of each cell (FIG. 8, STEP 4) was also used in our recent communications. Therefore, the surviving fraction of a population of N cells treated with Agent 1+Agent 2 is given by (FIG. 8, STEP 5):

$$SF_i(I'_{i1}, I'_{i2}) = \frac{1}{N}\left(\sum_{i=1}^{N} s_i\right) \tag{5A}$$

One embodiment of the invention employs a Monte Carlo approach to simulate the fate of each cell based on its experimentally determined drug uptake and used this information to calculate a surviving fraction for the entire cell population. The resulting surviving fractions were compared to experimentally determined values. Two different methods of predicting cell survival following a toxic insult were considered. The first approach addressed the role of individual agent uptake (i.e. cell fluorescence) in cell survival. The fate of individual cells can be determined based on their incorporation of a given agent, in this case daunomycin. However, it is worth noting that the magnitude of a cell's survival probability, per se, is not conclusive as to whether a cell survives or dies. Hence, there is a need to simulate the fate of each cell within the population using Monte Carlo techniques.

In FIG. 6, experimentally determined cell survival data are compared with theoretical cell survival data that were simulated by Monte Carlo analysis. However, before applying the Monte Carlo approach to account for the experimental lognormal uptake distributions, it is instructive to first see how this model behaves when each cell is assumed to contain the same uptake (i.e. the mean uptake). As expected, when theoretical survival is simulated assuming that each cell in the population contains an agent quantity corresponding to the net mean cellular fluorescence intensity, the resulting survival curve is monoexponential (FIG. 6, dashed lines). In this approach, the fact that each cell in the population is assumed to incorporate the same amount of agent implies $\sigma \to 0$. The data clearly show that, regardless of the agent, the theoretical survival derived from mean cellular fluorescence can recapitulate clonogenic survival only within the first exponential component of cell kill.

Figures 6A, 6B, 6C:
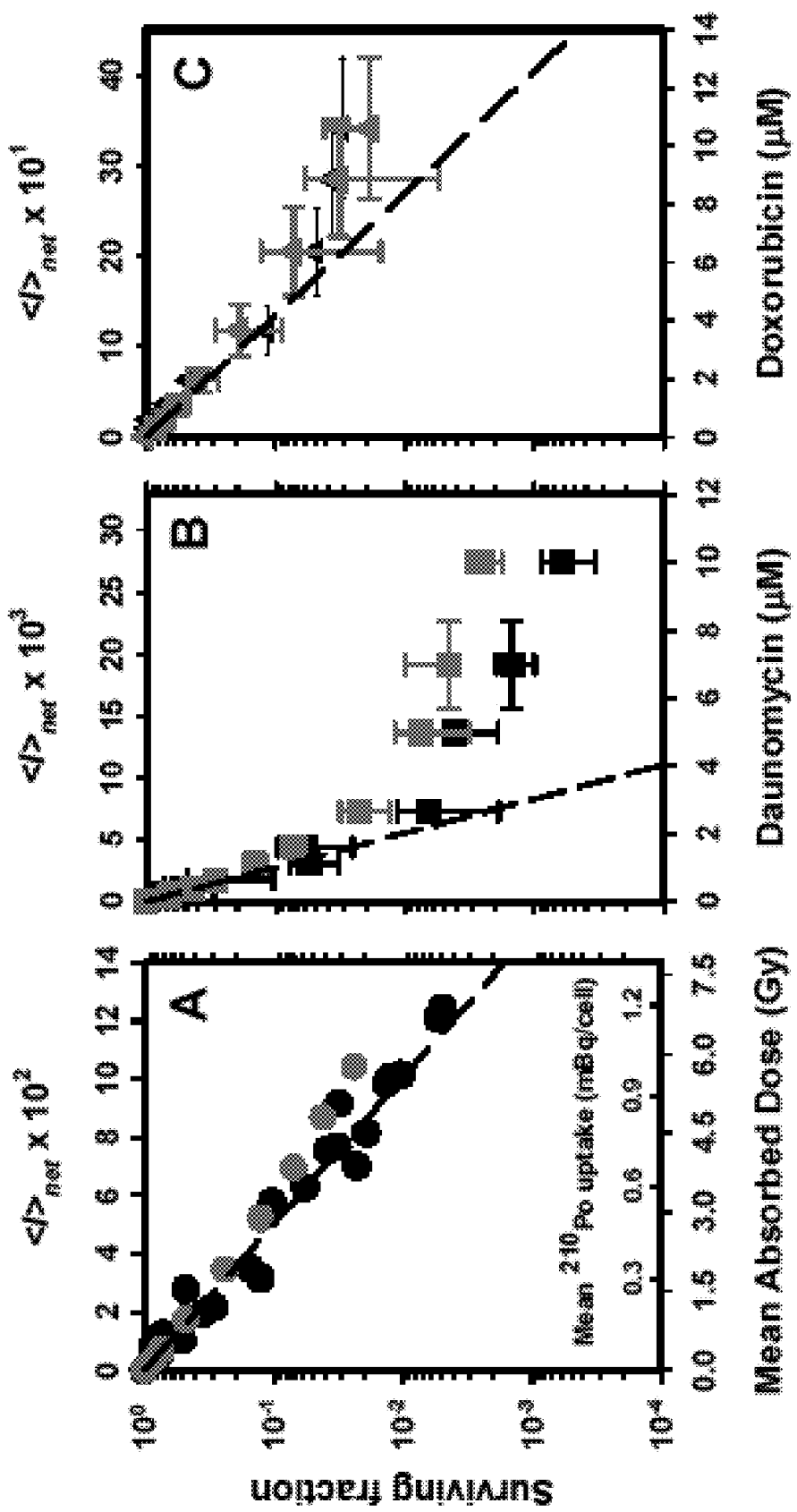
FIG. 6 shows comparison of Monte Carlo simulated cell survival (light symbols) with experimental clonogenic cell survival (black symbols) of V79 cells after treatment with (A) $^{210}$Po-citrate, (B) daunomycin, or (C) doxorubicin. The surviving fraction for $^{210}$Po-citrate are plotted against mean absorbed dose to the cell nucleus, mean intracellular $^{210}$Po activity, and mean fluorescence intensity of the europium tetracycline-citrate complex. Dashed lines represent Monte Carlo simulations of cell survival when every cell in the population is assumed to contain the same amount of drug that corresponds to the mean drug uptake for the respective extracellular concentration (i.e. net mean fluorescence intensity). Error bars represent the SE for <I>$_{net}$ based on fluorescence data from two and three independent experiments for daunomycin and doxorubicin, respectively. Error bars for $^{210}$Po citrate data are smaller than the symbols.
Figures 7A, 7B:
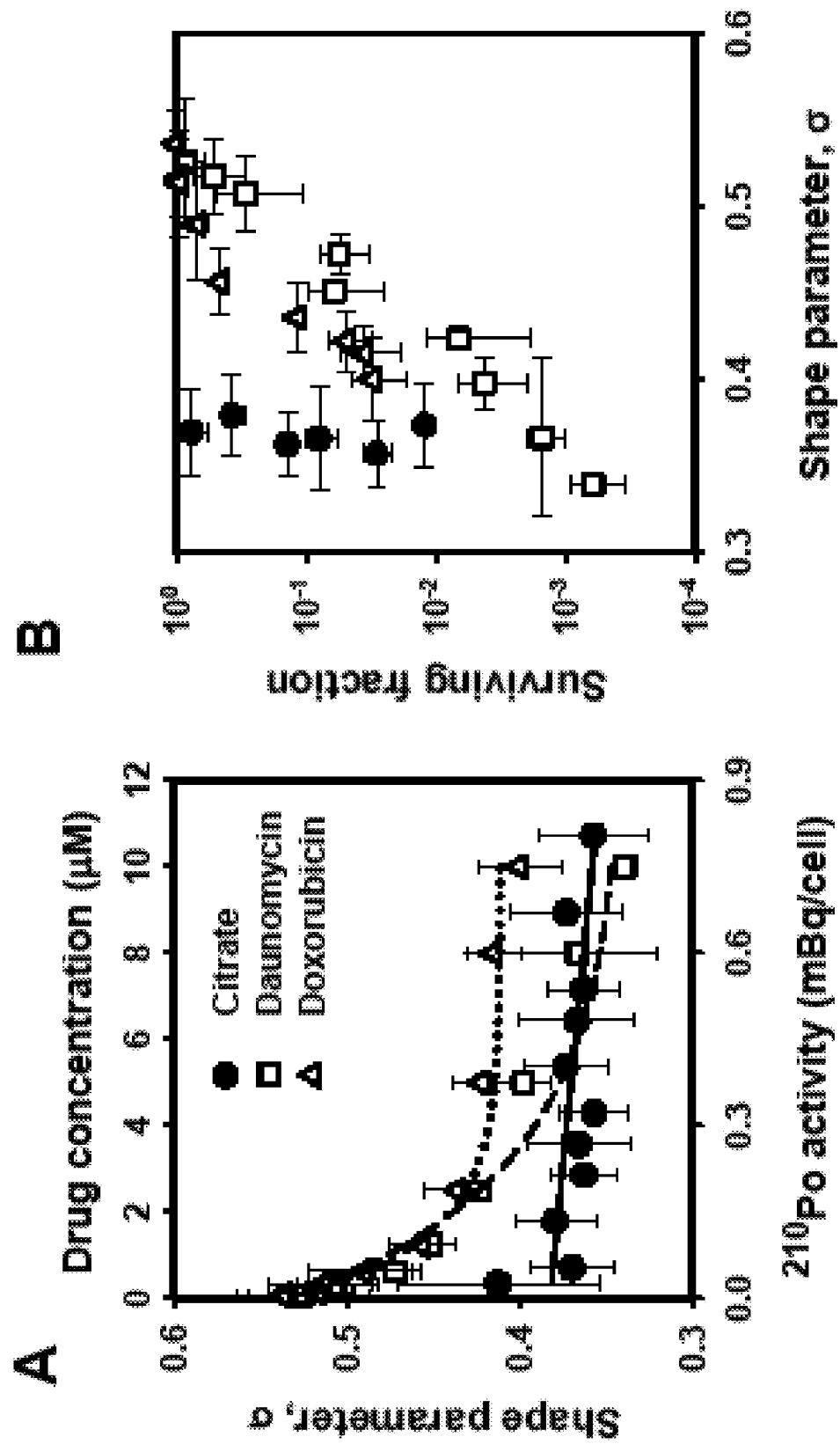
FIG. 7A displays the lognormal shape parameters σ for $^{210}$Po-citrate, daunomycin, and doxorubicin plotted against intracellular $^{210}$Po activity (•, solid line), and extracellular concentration of daunomycin (□, dashed line) and doxorubicin (Δ, dotted line), respectively. B displays the surviving fraction versus shape parameter for $^{210}$Po-citrate (•), daunomycin (□), and doxorubicin (Δ). Error bars represent SE of three independent experiments.

In contrast to the poor match between experimental data and the mean approach, Monte Carlo simulation of cell survival in a manner that accounts for the lognormal uptake distribution provides a very good prediction of clonogenic survival following treatment with $^{210}$Po-citrate, daunomycin, and doxorubicin (FIG. 6). Moreover, this model accurately predicts the transition between the first and second components of cell killing. This transition coincides with that observed when the lognormal shape parameter is plotted as a function of drug concentration. It should be noted that in the case of daunomycin, the Monte Carlo approach accurately predicts cell survival at low drug concentrations within the first log of cell kill but there is some deviation from experimental values at high drug concentrations (FIG. 6B). Nevertheless, the fit is remarkably good compared with the more conventional approach based on mean drug uptake (FIG. 6, dashed lines). Approaches based on mean uptake adequately predict the response in the low-dose realm, but fail to predict the upward trend in the survival curve that arises as a consequence of the lognormal distribution of drug uptake.

Toxicity of Cocktails

Figures 9A, 9B:
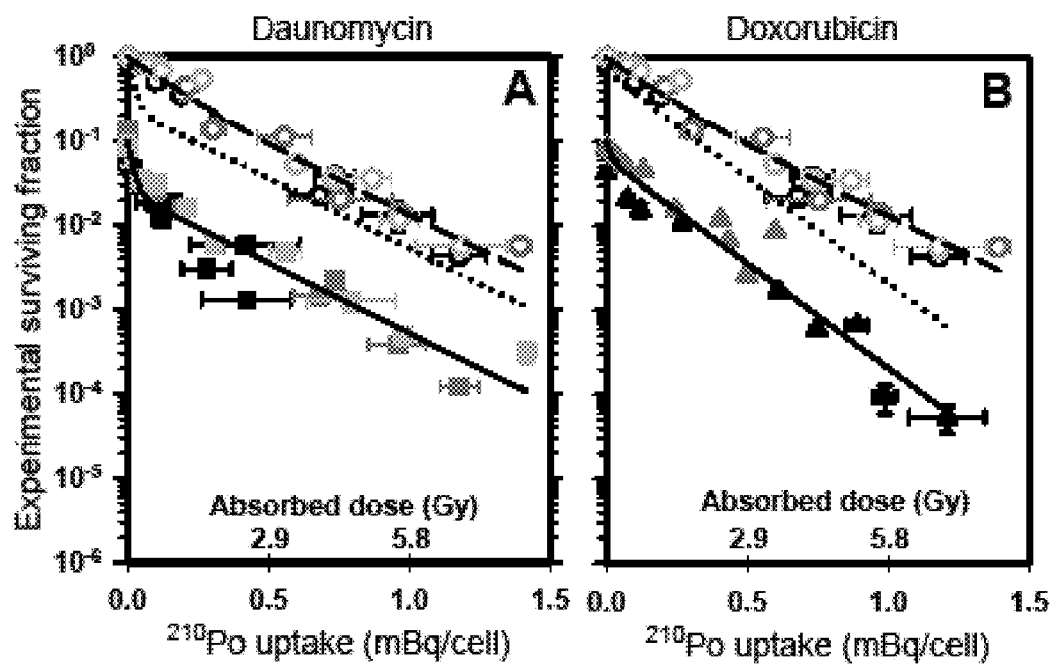
FIG. 9 displays the surviving fraction of V79 cells after treatment with graded amounts of $^{210}$Po-citrate in the absence or presence of: (A) 0.63 µM daunomycin or (B) 2.50 µM doxorubicin. Three independent experiments (○ $^{210}$Po-citrate; ■ $^{210}$Po-citrate+daunomycin; ▲ $^{210}$Po-citrate+doxorubicin). Dashed lines represent least-squares fits of data for $^{210}$Po-citrate to a 1-component exponential function. Solid curves represent least-squares fits of data for the combined treatment to 2-component exponential functions. Correction of the combined treatment curves for drug toxicity yielded the dotted curves. Horizontal and vertical error bars represent SE of mean cellular activity and surviving fraction of triplicate measurements, respectively. Some error bars are smaller than the symbols.

To evaluate cytotoxicity of combined treatment of V79 cells with $^{210}$Po-citrate and daunomycin, or $^{210}$Po-citrate and doxorubicin, the surviving fraction of clonogens was plotted as a function of mean cellular uptake of $^{210}$Po (FIG. 9) and as a function of mean absorbed dose to the cell nucleus. When cells were only treated with $^{210}$Po-citrate, the survival curve can be described by a 1-component exponential function. When cells were concomitantly treated with a single drug concentration and varying amounts of $^{210}$Po-citrate, the dose-response curves followed a 2-component exponential function. The data corresponding to the combined treatments were then corrected for drug toxicity, by dividing the surviving fraction for each datum point by the surviving fraction for drug alone (SF=0.10), and replotted in FIG. 9. Both of the corrected cell survival curves emerged below those obtained for $^{210}$Po-citrate alone. This indicates that daunomycin and doxorubicin enhance the radiotoxicity of α-particles in V79 cells. As illustrated in FIG. 9A, the enhancement of α-particle radiotoxicity by daunomycin was independent of radiation absorbed dose beyond about 0.5 Gy (~0.09 mBq/cell). On the other hand, the increased kill provided by doxorubicin showed a dose-dependent increase (FIG. 9B).

Figure 8:
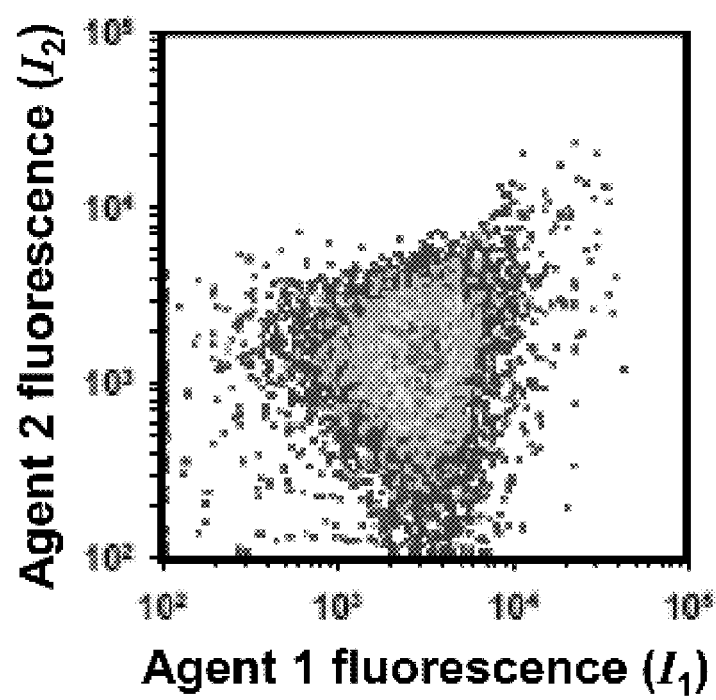
FIG. 8 shows a flow chart of the Monte Carlo procedure for determining fraction of surviving cells based on cellular fluorescence intensity distributions that arise after treatment of cells with a cocktail of two therapy agents (Agent 1 and Agent 2). In STEP 1, flow cytometry is used to obtain a fluorescence intensity dot-plot of the treated cells. STEP 2 calculates the probability $P(I_{i1}', I_{i2}')$ that the $i^{th}$ cell survives treatment with Agents 1 and 2, based on the respective normalized fluorescence intensities $I_{i1}'$ and $I_{i2}'$. A random number RAND$_i$ (0<RAND$_i$≤1) is then generated as depicted in STEP 3 by the dice. If RAND$_i$<$P(I_{i1}', I_{i2}')$, then the cell is scored as a survivor, otherwise it is considered dead (STEP 4). By repeating STEPS 1-4 for every cell, the surviving fraction for any sample population is calculated as illustrated in STEP 5.
Figures 10A, 10B:
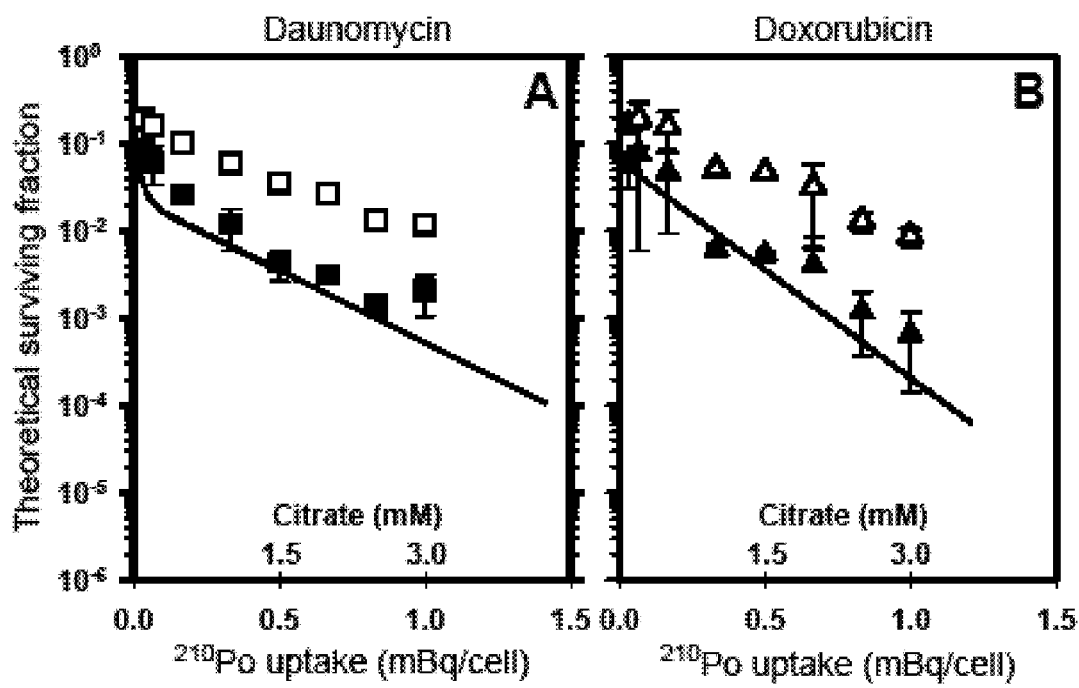
FIG. 10 displays the comparison of Monte Carlo simulated cell survival (symbols) with experimental clonogenic cell survival (solid curves) of V79 cells after treatment with combinations of (A) $^{210}$Po-citrate+0.63 µM daunomycin or (B) $^{210}$Po-citrate+2.50 µM doxorubicin. The experimental survival curves are least squares fits of the data presented in FIG. 9. Open and closed symbols represent Monte Carlo simulations of cell survival when the agents are assumed to act independently and interactively, respectively. Error bars represent the SE for simulated surviving fraction based on fluorescence data from two independent experiments for each cocktail. Some error bars are smaller than the symbols.

Predicting Cell Survival Based on Monte Carlo Analysis of Cellular Fluorescence Intensity The procedure depicted in FIG. 8 was used to assess the capacity of flow-cytometry assisted Monte Carlo simulation to recapitulate cell death and survival after exposure to $^{210}$Po-citrate+daunomycin or $^{210}$Po-citrate+doxorubicin. Following STEPS 2-4 of FIG. 8, application of Equations (6A), (8), (8A) and (4A) yields a plot of live and dead cells for fixed daunomycin concentration and varying concentrations of $^{210}$Po-citrate. The surviving fraction of a given cell population, based on normalized individual fluorescence intensities, $I_{ij}'$, was then calculated using Equation (5A) (FIG. 8, STEP 5). The symbols in FIG. 10 represent the theoretically modeled surviving fractions for $^{210}$P-citrate+daunomycin and $^{210}$P-citrate+doxorubicin. The theoretical data are superimposed on curves representing least squares fits to the experimental clonogenic survival data that were shown in FIG. 9. The open symbols were obtained assuming independent action of the agents (upper form of Equation (8A)), while closed symbols represent modeled cell survival when the agents are considered to interact (lower form of Equation (8A)). The Monte Carlo simulation that implemented agent-interaction is in excellent agreement with the experimental data.

These data provide experimental evidence that treatment of Chinese hamster V79 cells with a cocktail of $^{210}$Po-citrate and a chemotherapy drug (daunomycin or doxorubicin) causes cytotoxicity greater than expected based on the lethality of the agents when used alone (FIG. 9). These data show that when the effect of each chemotherapy drug is corrected for, the corrected survival curves do not coincide with that for the $^{210}$Po alone treatment. The curves emerge below the $^{210}$Po survival curve. This is indicative of a chemical enhancement of α-particle radiotoxicity, or perhaps that cells that are not adequately labeled with $^{210}$Po-citrate (e.g. low end of the lognormal uptake distribution) are killed by the chemotherapy drug. The flow-cytometry assisted Monte Carlo simulation of cell survival can distinguish these possibilities.

In the cocktail embodiment, the flow cytometry-assisted Monte Carlo model has been applied to agent-incorporation data obtained after treating cells with a cocktail of $^{210}$Po-citrate+daunomycin or $^{210}$Po-citrate+doxorubicin. The test of the capacity of this approach to predict the cytotoxicity of a combination therapy is presented in FIG. 10 where experimentally determined cell survival curves (solid curves) are compared with theoretical cell survival as simulated by Monte Carlo analysis (symbols). When it is assumed that the agents act independently, the model fails to predict clonogenic cell survival (FIG. 10, open symbols). However, when the agents are assumed to interact, the Monte Carlo simulation predicts cell survival exquisitely at all intracellular activities of $^{210}$Po (FIG. 10, closed symbols). This suggests that, at the levels of cell kill observed, the chemotherapy agents provide a chemical enhancement of the α-particle radiotoxicity in V79 cells rather than killing cells that are inadequately labeled with $^{210}$Po-citrate. The latter possibility may become important at very high levels of cell kill (i.e. 5 or 6 logs of kill).

The cocktail approach accurately predicts the experimental toxicity of the $^{210}$Po-citrate+daunomycin/doxorubicin cocktails based only on knowledge of the initial slope of the dose-response curves for each agent (i.e. $<I_j>_{37,net}$) and the cellular uptake distribution of the ingredients of the cocktail. This can be extremely helpful in designing more effective cocktails for targeted therapy; these cocktails may consist of a sizeable number of agents.

Although the use of α-emitting radionuclides in radioimmunotherapy has gained considerable interest, the relatively high potency of α-particles limits the amount of activity that can be administered. To benefit from the potency of α-particles and yet maintain low normal tissue toxicity, the use of low doses of cocktails of α-particle based radioimmunotherapeutics and chemotherapy drugs that effectively target all malignant cells is warranted. Yet, only one study has been reported to demonstrate enhancement of the anti-tumor effects of α-particles in a mouse tumor model by paclitaxel. While the exact mechanism of that enhancement is not known, it was suggested to be dependent on the sequence of the administration of the therapeutic agents, and was both angiogenic and apoptotic by nature. Predicting response to radionuclide therapy and chemotherapy drugs on a cell-by-cell basis enables the dissecting of mechanisms involved with drug interaction, and thereby improves the design of more effective cocktails for targeted therapy. Therefore, it is possible that agents previously discarded on the basis of single-agent toxicity may become key ingredients in a cocktail by virtue of their capacity to target a few cells that only incorporate small amounts of the primary drug.

Of particular importance in the above-described embodiments is the fact that the flow-cytometry assisted Monte Carlo simulation of cell survival requires knowledge of only the initial slope of the dose-response curve (i.e. $<I>_{net,37}$) and the uptake distribution of the radiopharmaceutical or drug. With these two pieces of information, the entire clonogenic survival curve can be recapitulated including both the 1- or 2-component exponential shapes. The approach applies equally well for drugs that are not likely to be characterized by a lognormal uptake distribution such as Hoechst 33342, whose uptake is directly proportional to DNA content.

Special attention should be given to the process of normalizing the fluorescence data obtained by flow cytometry. The measured fluorescence intensities are dependent on flow cytometry hardware (e.g. laser wavelength and intensity), settings (e.g. amplification), etc. Given that the fluorescence intensity is ultimately related to drug uptake in terms of quantities such as mass (g) and/or activity (Bq), there will be a need to implement calibrations for these quantities. The mean activity per cell can be readily measured with high accuracy and precision using standard radiation detection devices. This information, along with the distribution of cellular fluorescence intensities, provides detailed knowledge of the activity in each cell of the population. Furthermore, calibration with drugs with known specific activity (Bq/g) can provide detailed knowledge of the mass of drug in each cell of the population. Accordingly, survival probabilities might be represented by $$P_i = e^{-\frac{m_i}{\langle m \rangle_{37}}} \text{ and } e^{-\frac{a_i}{\langle a \rangle_{37}}},$$

respectively, where the mass of drug in the cell, $m_i = \xi I_i'$ and/or the amount of radioactivity in the cell $a_i = \kappa I_i'$. The constants $\xi$ and $\kappa$ represent the slopes of plots of $<m>$ and $<a>$ versus $<I>_{net}$, respectively. These probabilities would be independent of flow cytometry hardware and instrument settings.

Not specifically addressed are the underlying reasons why the experimental and Monte Carlo derived clonogenic survival curves deviate most from those for an average concentration of agent at the higher concentrations. Although not wishing to be bound by any theory, in the realm of chemotherapy, this is often ascribed to resistant subpopulations that may express high levels of the multidrug resistant protein MDR1. One function of this protein is to facilitate the active removal of toxins from the cell, thereby foiling its therapeutic intent. Low cellular uptake by some cells within a population is also especially important for receptor-targeted agents such as radiolabeled antibodies used for radioimmunotherapy. The number of receptors on a given cell can vary widely over a cell population such that sublethal activity may be taken up by a subpopulation. The flow cytometry assisted Monte Carlo embodiment described above can be extremely useful in modeling the consequence of such nonuniformities, thereby reducing the level of experimental effort that is needed to optimize a therapy. Furthermore, a variety of other capabilities can be built into the model to account for other toxic insults to the cell population such as cross-dose received from radiations emitted by neighboring cells, and radiation- or chemically-induced bystander effects.

The use of flow cytometry to predict clonogenic survival using either agent-negative subpopulations of cells or flow cytometry-assisted Monte Carlo simulation has been demonstrated in the present disclosure. Generally, the fraction of apparently agent-negative cells cannot predict cell survival as determined by colony forming ability. However, it has been demonstrated that Monte Carlo simulation using cellular agent incorporation based on individual cell fluorescence intensity of therapeutic agents is a suitable predictor of cell survival. This flow cytometry based approach, which takes explicit account of the lognormal distribution of cellular uptake of the agents, offers a rapid means for determining treatment response on a cell-by-cell basis, and is invaluable in the selection of agents for the design of highly effective therapeutic cocktails that are capable of targeting the diversity in tumor cell populations. Such cocktails can be created not only for treatment of cancer, but also for infectious diseases and other diseases that may be amenable to targeted therapies. Furthermore, the single-cell Monte Carlo embodiment can be used to resolve difficulties encountered when attempting to predict biological response at the multicellular level using macroscopic mean agent doses.

The invention has been described via the specific embodiments and examples provided above which, however, do not limit the invention in any way.

What is claimed is:

1. A 2-stage targeting method of treating a disease or condition for a patient in need thereof, said method comprising:
   (1) identifying and providing a plurality of candidate cell-specific agents relevant to the disease or condition of said patient, wherein said cell-specific agents are two-stage agents comprising:
      (a) one or more Stage 1 targeting agents which target diseased or affected cells of said patient; and
      (b) one or more Stage 2 binding agents which bind to said Stage 1 targeting agents and are capable of carrying at least one additional agent selected from the group consisting of toxins, radionuclides and fluorochromes, wherein each Stage 2 binding agent can only bind to a single corresponding Stage 1 targeting agent;
   (2) injecting said patient with a cocktail of Stage 1 targeting agents via a route appropriate to said disease or condition, and allowing sufficient time for maximum uptake by said diseased or affected cells and substantial clearance of unbound Stage 1 targeting agents;
   (3) withdrawing a sample of said patient's diseased or affected cells loaded with Stage 1 targeting agents;
   (4) treating said sample of said cells in vitro with a cocktail of Stage 2 binding agents, wherein each Stage 2 binding agent in the cocktail carries at least one additional agent which is a unique fluorochrome, and wherein said Stage 2 binding agents bind to said Stage 1 targeting agents loaded into said cells;
   (5) quantifying the amount of each Stage 2 binding agent binding to each diseased or affected cell using fluorescence spectroscopy to provide quantitative measured binding data, and plotting the number of cells versus the amount of bound Stage 2 binding agent to obtain distribution plots for said cells;
   (6) predicting the response of said diseased or affected cells for every possible combination of Stage 1 targeting agents and Stage 2 binding agents using a Monte Carlo simulation that uses (i) said measured binding in each cell of said Stage 2 binding agent carrying a fluorochrome as the additional agent, and (ii) a function that represents the probability that a given cell will survive upon binding a given amount of an armed Stage 2 binding agent carrying a toxin and/or radionuclide as the additional agent; and (a) identifying the predicted optimal combination of said armed Stage 2 binding agents when said cells are exposed to increasing concentrations of a plurality of armed Stage 2 binding agents, (b) identifying the predicted optimal concentration of each armed Stage 2 binding agent for said patient, and (c) said Monte Carlo simulation accounts for the predicted amount of each armed Stage 2 binding agent in each cell;

(7) arming each Stage 2 binding agent of said predicted optimal combination with one or more therapeutic agents selected from the group consisting of toxins, radionuclides, and combinations of two or more thereof, to form an armed cocktail;

(8) optionally, repeating step (2); and (9) injecting said armed cocktail into said patient.

2. The method of claim 1, further comprising repeating steps (3) through (6) with healthy cells of said patient to assess uptake of said Stage 1 targeting agents and Stage 2 binding agents in each healthy cell.

3. The method of claim 1, wherein said individual patient's cells comprise cancer cells.

4. The method of claim 1, wherein said incorporation of said therapeutic agent is measured using a high-speed technique.

5. The method of claim 4, wherein said high-speed technique comprises fluorescence spectroscopy.

6. The method of claim 5, wherein the fluorescence measurement comprises the mean fluorescence intensity (MFI).

7. The method of claim 4, wherein the high-speed technique for assaying therapeutic agent incorporation on a cell-by-cell basis comprises flow cytometry.

8. The method of claim 3, wherein the high-speed technique for assaying therapeutic agent incorporation on a cell-by-cell basis comprises fluorescence microscopy or laser scanning microscopy.

9. The method of claim 1, wherein said Monte Carlo simulation comprises flow-cytometry-assisted Monte Carlo simulation.

10. The method of claim 1, wherein said Monte Carlo simulation comprises fluorescence microscope-assisted Monte Carlo simulation or laser scanning microscope-assisted Monte Carlo simulation.

* * * * *